United States Patent
Thuren et al.

(10) Patent No.: US 10,975,145 B2
(45) Date of Patent: *Apr. 13, 2021

(54) METHODS OF REDUCING THE RISK OF EXPERIENCING A CARDIOVASCULAR (CV) EVENT OR A CEREBROVASCULAR EVENT IN A PATIENT THAT HAS SUFFERED A QUALIFYING CV EVENT

(71) Applicant: Novartis AG, Basel (CH)

(72) Inventors: Tom Thuren, Succasunna, NJ (US); Andrew Zalewski, Elkins Park, PA (US); Michael Shetzline, Randolph, NJ (US)

(73) Assignee: Novartis AG, Basel (CH)

(*) Notice: Subject to any disclaimer, the term of this patent is extended or adjusted under 35 U.S.C. 154(b) by 110 days.

This patent is subject to a terminal disclaimer.

(21) Appl. No.: 15/483,619

(22) Filed: Apr. 10, 2017

(65) Prior Publication Data
US 2017/0275358 A1    Sep. 28, 2017

Related U.S. Application Data

(63) Continuation of application No. 14/347,071, filed as application No. PCT/US2012/057444 on Sep. 27, 2012, now Pat. No. 9,683,038.

(60) Provisional application No. 61/541,341, filed on Sep. 30, 2011.

(51) Int. Cl.
C07K 16/24    (2006.01)
A61K 39/00   (2006.01)

(52) U.S. Cl.
CPC ...... *C07K 16/245* (2013.01); *A61K 2039/505* (2013.01); *A61K 2039/545* (2013.01); *C07K 2317/21* (2013.01)

(58) Field of Classification Search
None
See application file for complete search history.

(56) References Cited

U.S. PATENT DOCUMENTS 9,683,038 B2    6/2017  Thuren et al.
2010/0316651 A1* 12/2010  Scannon ............ C07K 16/245
                                              424/158.1

FOREIGN PATENT DOCUMENTS

WO        0216436 A2    2/2002
WO        2010 138939   12/2010

OTHER PUBLICATIONS

Ridker et al., "Interleukin-1 inhibition and the prevention of recurrent cardiovascular events: Rationale and Design of the Canakinumab Ant-inflammatory Thrombosis Outcomes Study (CANTOS)", American Heart Journal, Mosby—Year Book Inc. US, vol. 162, No. 4, pp. 597-605, Sep. 14, 2011.

(Continued)

*Primary Examiner* — Gary B Nickol
*Assistant Examiner* — Jegatheesan Seharaseyon
(74) *Attorney, Agent, or Firm* — Meghan S. Adams

(57) ABSTRACT

The present invention relates to an IL-1β binding antibody or a functional fragment thereof for use in preventing or reducing risk of experiencing a recurrent cardiovascular (CV) event or a cerebrovascular event in a patient that has suffered of a qualifying CV event.

21 Claims, 9 Drawing Sheets

Specification includes a Sequence Listing.

(56) References Cited

OTHER PUBLICATIONS

Ridker et al., "High-sensitivity C-reactive protein, vascular imaging, and vulnerable plaque: more evidence to support trials of anti inflammatory therapy for cardiovascular risk reduction", Circulation. Cardiovasuclar Imaging vol. 4, No. 3, pp. 195-197, May 2011.
Rieke et al., "The human anti-IL1̂monoclonal antibody ACZ885 is effective in joint inflammation models in mice and in a proof-of-concept study in patients with rheumatoid arthritis", Arthritis Research and Therapy, Biomed Central, London, vol. 10, No. 3, pp. 1-9, Jun. 5, 2008.
Owyan, et al., "XOMA 052, a potent, high affinity monoclonal antibody for the treatment of IL-1 beta-mediated diseases", MABS, vol. 3, No. 1, pp. 49-60, Jan. 2011.
Health Canada, "Summary Basis of Decision (SBD) Pr ILARIS", Health Products and Food Branch, pp. 1-21, Jul. 19, 2010.
Abbate et al., "C-reactive protein and other inflammatory biomarkers as predictors of outcome following acute coronary syndromes", Seminars in Vascular Medicine, vol. 3, No. 4, pp. 375-384, Nov. 2003.
Hamm and Klootwijk (1999) Lancet 353 (suppl II):10-15.
Cosentyx® Product Insert, dated Jan. 2016.
Taltz® Product Insert, dated Mar. 2016.
Toss et al. (1997) Circulation 96:4204-10.
Lindahl et al. (2000) NEJM 343:1139-47.
Pearson et al. (2003) Circulation 107:499-511.
Versaci et al. (2000) Am J. Cardio. 85 :92-94.
Pflieger et al. (2011) Am. Fam Physician 83:819-826.
McMurray et al. (2009) Circulation 120:2188-96.
Ridker (2005) NEJM 352 :20-8.
Ridker et al. (2008) NEJM 359 :2195-207.
Thygesen et al (2007) Circulation; 116:2634-2653.
Fournier et al., "The High-Sensitivity C-Reactive Protein Level One Month After Bare-Metal Coronary Stenting May Predict Late Adverse Events", Rev. Esp. Cardiol., vol. 61, No. 3, pp. 313-316, 2008.
Portolano et al., "Lack of promiscuity in autoantigen-specific H and L chain combinations as revealed by human H and L chain 'roulette'", Journal of Immunology, 1993, vol. 150, No. 3, pp. 880-887.
Clackson et al., "Making antibody fragments using phage display libraries", Nature, 1991, vol. 352, pp. 624-628.
Sponsor: Novartis Pharmaceuticals. Cardiovascular Risk Reduction Study (Reduction in Recurrent Major CV Disease Events) (CANTOS). NIH U.S. National Library of Medicine. https://clinicaltrials.gov/ct2/show/NCT01327846?term=NCT01327846&rank=1 Accessed on Jan. 2, 2019. First published/posted: Apr. 4, 2011. 10 pages.

* cited by examiner

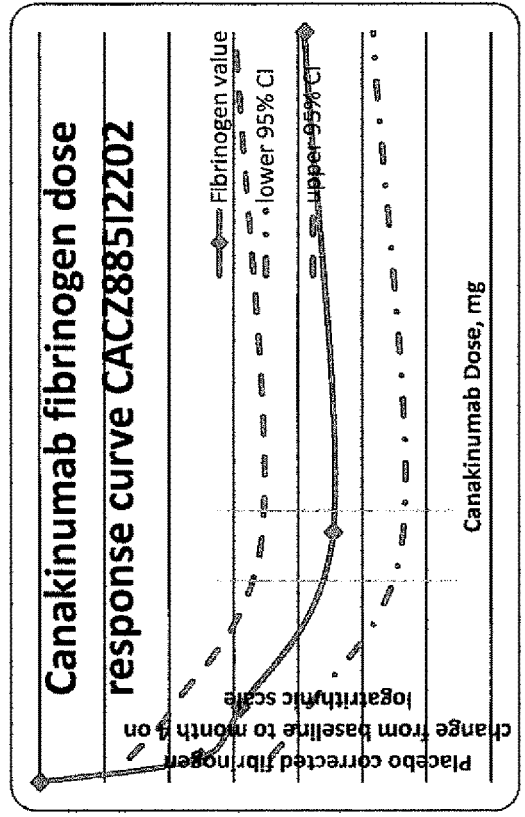
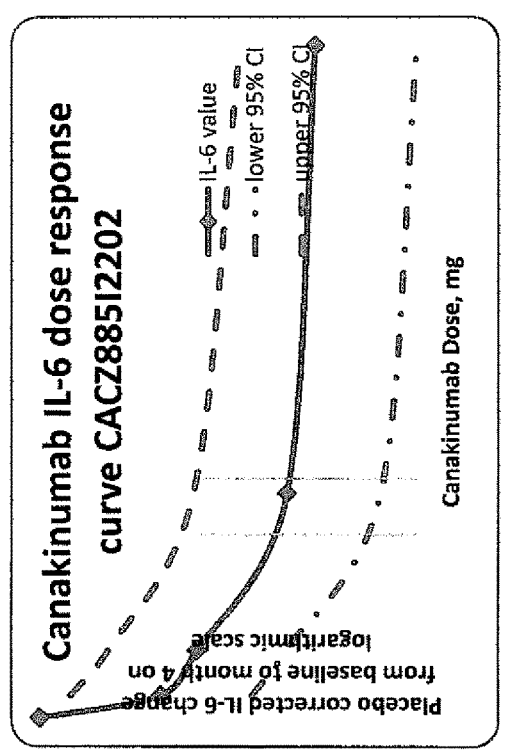
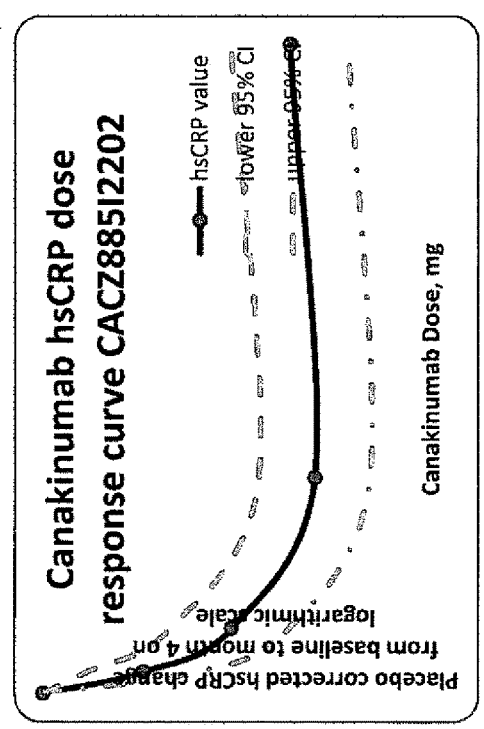
Fig. 5

```
            ATGGAGTTTGGGCTGAGCTGGGTTTTCCTCGTTGCTCTTTTAAGAGGTGTCCAGTGTCAG
    -19     M  E  F  G  L  S  W  V  F  L  V  A  L  L  R  G  V  Q  C  Q    - 1

GTGCAGCTGGTGGAGTCTGGGGGAGGCGTGGTCCAGCCTGGGAGGTCCCTGAGACTCTCC
            V  Q  L  V  E  S  G  G  G  V  V  Q  P  G  R  S  L  R  L  S    - 21

TGTGCAGCGTCTGGATTCACCTTCAGTGTTTATGGCATGAACTGGGTCCGCCAGGCTCCA
            C  A  A  S  G  F  T  F  S  V  Y  G  M  N  W  V  R  Q  A  P    - 41

GGCAAGGGGCTGGAGTGGGTGGCAATTATTTGGTATGATGGAGATAATCAATACTATGCA
            G  K  G  L  E  W  V  A  I  I  W  Y  D  G  D  N  Q  Y  Y  A    - 61

GACTCCGTGAAGGGCCGATTCACCATCTCCAGAGACAATTCCAAGAACACGCTGTATCTG
            D  S  V  K  G  R  F  T  I  S  R  D  N  S  K  N  T  L  Y  L    - 81

CAAATGAACGGCCTGAGAGCCGAGGACACGGCTGTGTATTATTGTGCGAGAGATCTTAGG
            Q  M  N  G  L  R  A  E  D  T  A  V  Y  Y  C  A  R  D  L  R    - 101

ACTGGGCCTTTTGACTACTGGGGCCAGGGAACCCTGGTCACCGTCTCCTC
            T  G  P  F  D  Y  W  G  Q  G  T  L  V  T  V  S  S                - 118
```

Italics: Leader sequence (not in mature antibody)

Bold and underlined : CDR's

Fig. 7

```
    ATGTTGCCATCACAACTCATTGGGTTTCTGCTGCTCTGGGTTCCAGCCTCCAGGGGTGAA
-19  M  L  P  S  Q  L  I  G  F  L  L  W  V  P  A  S  R  G  E    - 11

ATTGTGCTGACTCAGTCTCCAGACTTTCAGTCTGTGACTCCAAAGGAGAAAGTCACCATC
     I  V  L  T  Q  S  P  D  F  Q  S  V  T  P  K  E  K  V  T  I  - 21

ACCTGCCGGGCCAGTCAGAGCATTGGTAGTAGCTTACACTGGTACCAGCAGAAACCAGAT
     T  C  R  A  S  Q  S  I  G  S  S  L  H  W  Y  Q  Q  K  P  D  - 41

CAGTCTCCAAAGCTCCTCATCAAGTATGCTTCCCAGTCCTTCTCAGGGGTCCCCTCGAGG
     Q  S  P  K  L  L  I  K  Y  A  S  Q  S  F  S  G  V  P  S  R  - 61

TTCAGTGGCAGTGGATCTGGGACAGATTTCACCCTCACCATCAATAGCCTGGAAGCTGAA
     F  S  G  S  G  S  G  T  D  F  T  L  T  I  N  S  L  E  A  E  - 81

GATGCTGCAGCGTATTACTGTCATCAGAGTAGTAGTTTACCATTCACTTTCGGCCCTGGG
     D  A  A  A  Y  Y  C  H  Q  S  S  S  L  P  F  T  F  G  P  G  - 101

ACCAAAGTGGATATCAAA                                            - 107
     T  K  V  D  I  K
```

Italics: Leader sequence (not in mature antibody)

Bold and underlined: CDR's

Fig. 8

METHODS OF REDUCING THE RISK OF EXPERIENCING A CARDIOVASCULAR (CV) EVENT OR A CEREBROVASCULAR EVENT IN A PATIENT THAT HAS SUFFERED A QUALIFYING CV EVENT

RELATED APPLICATIONS

The present disclosure claims priority to U.S. Provisional Patent Application No. 61/541,341, filed Sep. 30, 2011, the disclosure of which is incorporated by reference herein in its entirety.

TECHNICAL FIELD

The present disclosure relates to novel uses and regimens for preventing or reducing risk of experiencing a recurrent cardiovascular (CV) event or a cerebrovascular event in a patient that has suffered of a qualifying CV event, which employ an IL-1β binding antibody or functional fragments thereof, e.g., canakinumab.

BACKGROUND OF THE DISCLOSURE

Atherosclerosis is a disease characterized by chronically high inflammatory state. Arterial inflammation and endothelial dysfunction play key roles at all stages of the atherothrombotic process. Inflammatory mediators are intimately implicated with the cascade of events leading to atherosclerotic plaque initiation, progression and rupture. Vascular endothelial cells express a variety of adhesion molecules that recruit monocytes when chronically exposed to noxious stimuli or pathological conditions. Adverse conditions such as hyperlipidemia are associated with enrichment of a pro-inflammatory subset of monocytes. These monocytes apparently enter the intima under the influence of chemotactic stimuli and engulf modified low density lipoprotein (LDL) and cholesterol crystals (Duewell et al 2010). The material internalized by phagocytes induces phagolysosomal damage and subsequent leakage of contents into cytosol to activate inflammasomes and caspase 1, and consequently the generation of interleukin-1b (IL-1β) from pro-interleukin-1β.

Interleukins are key mediators in the chronic vascular inflammatory response in cardiovascular (CV) disease and have been demonstrated in animal models and in humans to be potent modulators of pro-inflammatory processes. The fact that these cytokines and their receptors are highly expressed and are functional in almost all cell types implicated in the pathogenesis of atherosclerosis including smooth muscle cells, certain subset of macrophages and T cells as well as endothelium support the role of interleukins in vascular disease. For example, IL-1β is a potent smooth muscle cell mitogen, an activator of endothelial cells and increases extra cellular matrix and collagen deposition, which plays a role in plaque burden and arterial thickening. Furthermore, lack of IL-1β or ablation of IL-1 receptor has been shown to decrease severity of atherosclerosis in apoE deficient mice. Thus, antagonism of the IL-1β mediated inflammation is a primary and attractive target for ameliorating the vessel wall inflammation associated with atherosclerosis.

WO2010/138939 generally relates to a method of treating cardiovascular disorders with an IL-1β antibody. However it does not disclose a method of preventing or reducing risk of recurrent CV events or a cerebrovascular event.

SUMMARY OF THE DISCLOSURE

Inflammation contributes to all phases of the atherothrombotic process and patients with elevated inflammatory biomarkers such as hsCRP have increased vascular risk. The present disclosure relates, in part, to the finding that direct inhibition of inflammation by administration of IL-1β binding antibodies will reduce cardiovascular event rates.

Accordingly, the present disclosure is directed to a method of preventing or reducing risk of experiencing a recurrent cardiovascular (CV) event or a cerebrovascular event in a patient that has suffered of a qualifying CV event, comprising administering about 25 mg to about 300 mg of an IL-1β binding antibody or functional fragment thereof, wherein said patient has a level of hsCRP of about ≥1 mg/L before administration of said antibody or functional fragment thereof.

Further features and advantages of the disclosure will become apparent from the following detailed description of the invention.

IL-1β=interleukin-I beta; IL-1R=interleukin-1 receptor; IL-1Ra=interleukin-1 receptor antagonist; CAPS=cryopyrin-associated periodic syndrome; MWS=Muckle-Wells Syndrome; NOMID=neonatal-onset multi-system inflammatory disease.

Figure 1:
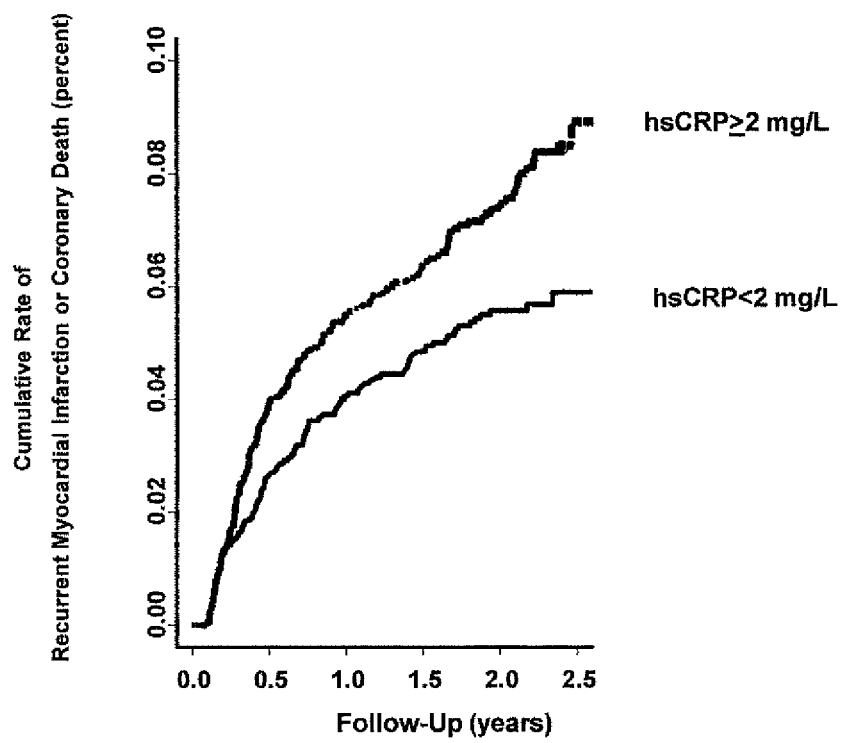
FIG. 1: Risk of recurrent cardiovascular events in the PROVE IT-TIMI 22 trial of acute coronary syndrome patients after initiation of statin therapy, according to on-treatment levels of hsCRP. Adapted from Ridker P M, Cannon C P, Morrow D, Rifai N, Rose L M, McCabe C H, Pfeffer M A, Braunwald E. C-reactive protein levels and outcomes after statin therapy. N Engl J Med 2005; 352:20-8.
Figure 2:
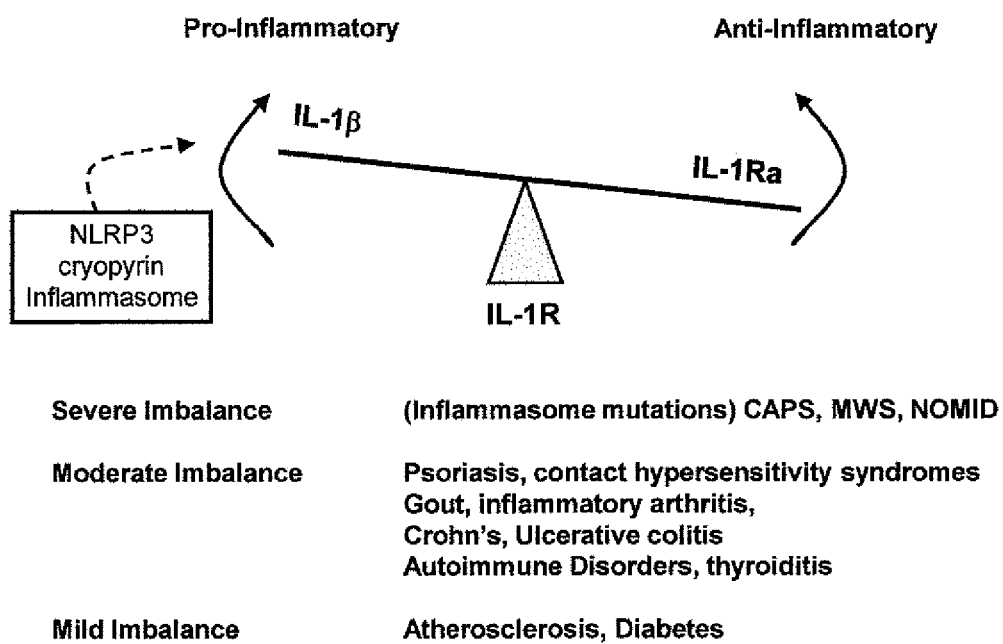
FIG. 2: Balancing the IL-1β system and its contributions to human disease.
Figure 3:
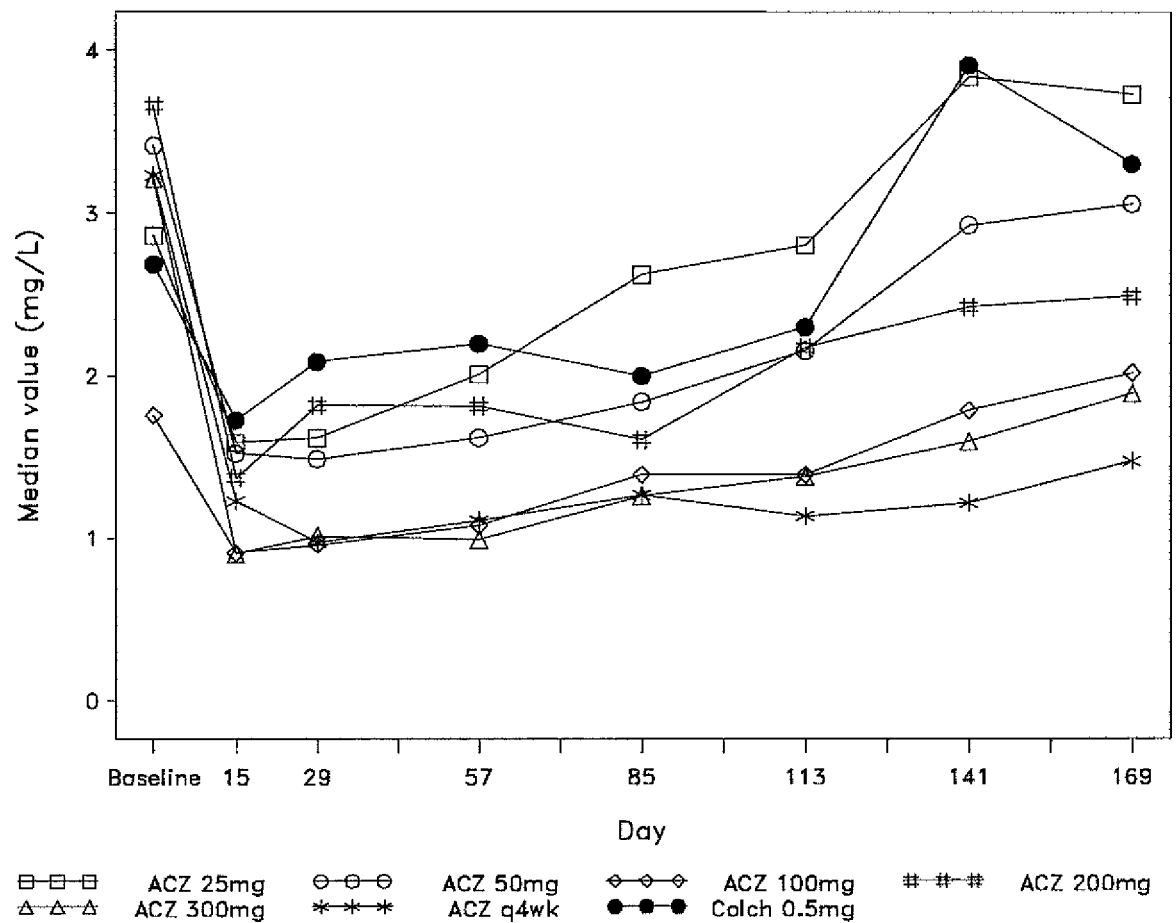
Figure 4:
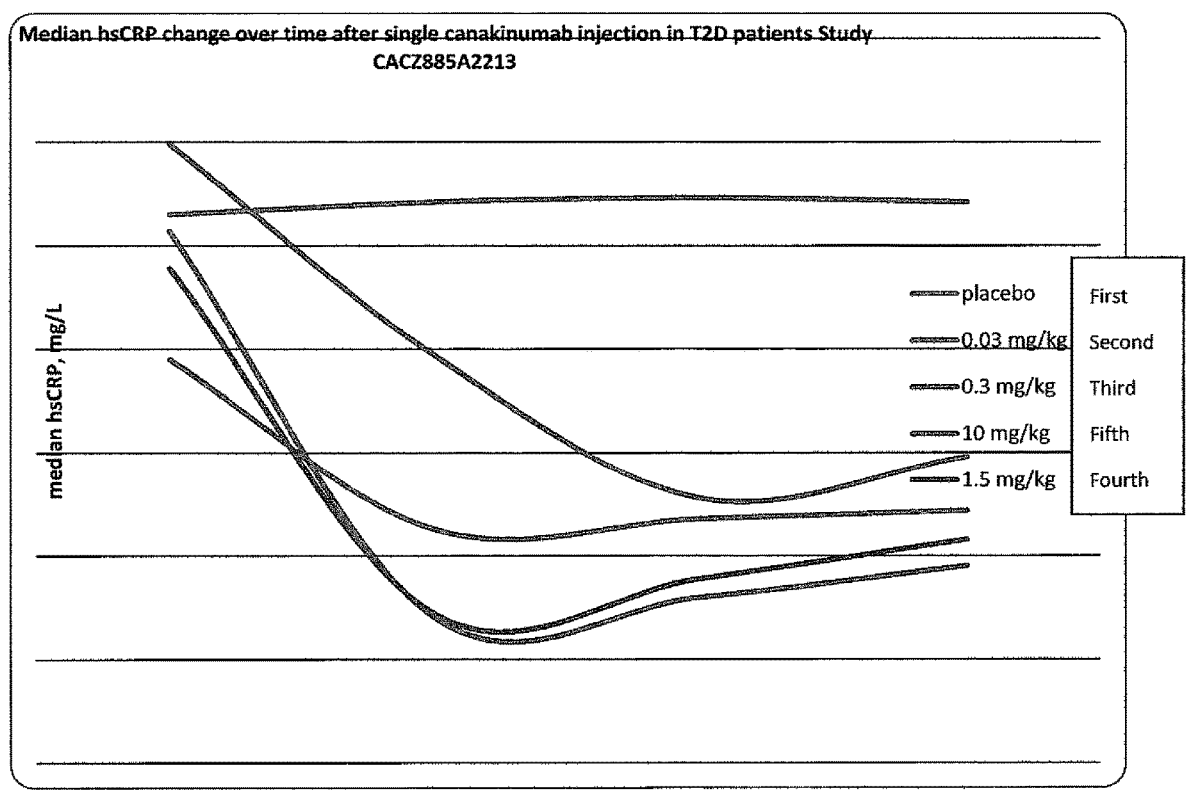

FIG. 3: hsCRP lowering by canakinumab in gout patients supports quarterly dosing regimen (study H2251): the figure shows hsCRP lowering by a single canakinumab dose is durable for 3 months (85 days).
ACZ=ACZ885=canakinumab
Colch=colchicine FIG. 4: Quarterly dosing regimen is supported by study CACZ885A2213 data on patients with T2DM. X axis indicates time in days (d)

FIG. 5: Multiple lines of evidence confirm dose and regimen selection increasing confidence and biological plausibility.

Figure 6:
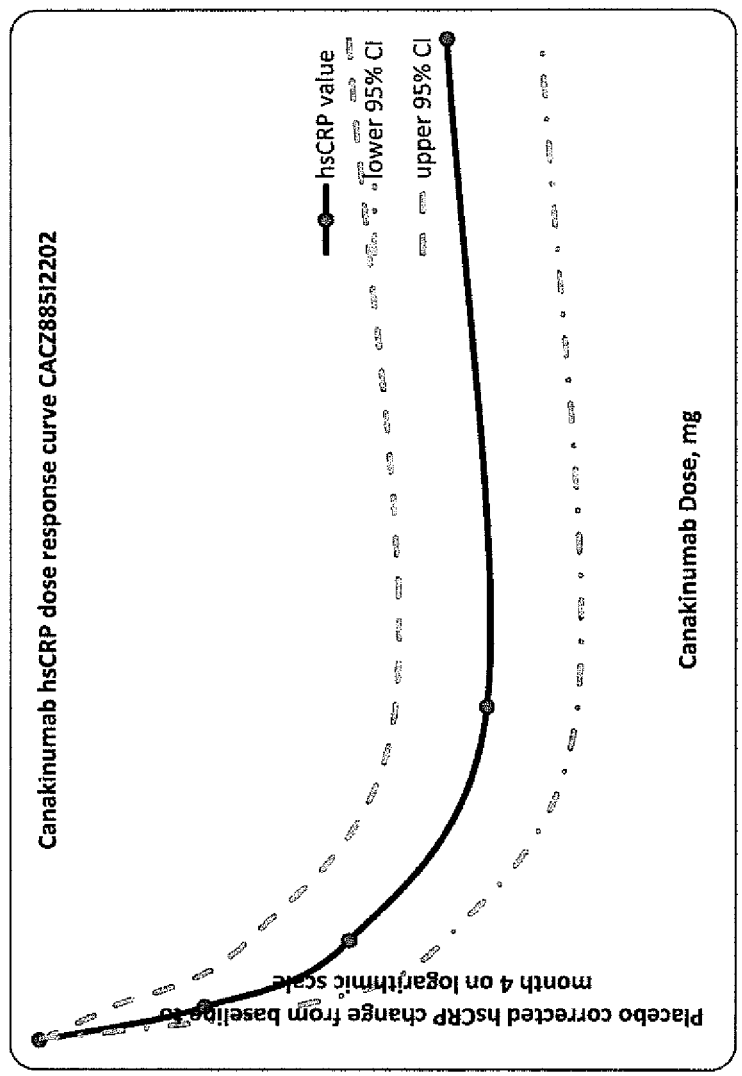

FIG. 6: Phase II study data on hsCRP response supports selection of 15 and 50 mg monthly doses of canakinumab
  Biological activity of canakinumab can be monitored using hsCRP as a surrogate
  Canakinumab dose selection based on primary analysis data from study 12202 (5 to 150 mg vs. placebo monthly, 16 weeks, N=524):
    Safety (general safety and lipid effects)
    hsCRP lowering dose response characteristics
    15 mg monthly dose of canakinumab was selected as a sub-maximal dose (30% hsCRP lowering and 95% upper CI<0)
    50 mg monthly dose of canakinumab as maximally efficacious dose (40% hsCRP lowering)

FIG. 7: The amino-terminal sequences of the heavy chain variable domain ($V_H$) and the corresponding DNA sequences of canakinumab are given, in which the CDRs are shown in bold type and underlined, and leader sequence in italics.

FIG. 8: The amino-terminal sequences of the light chain variable domain ($V_L$) and the corresponding DNA sequences of canakinumab are given, in which the CDRs are shown in bold type and underlined, and leader sequence in italics.

Figure 9:
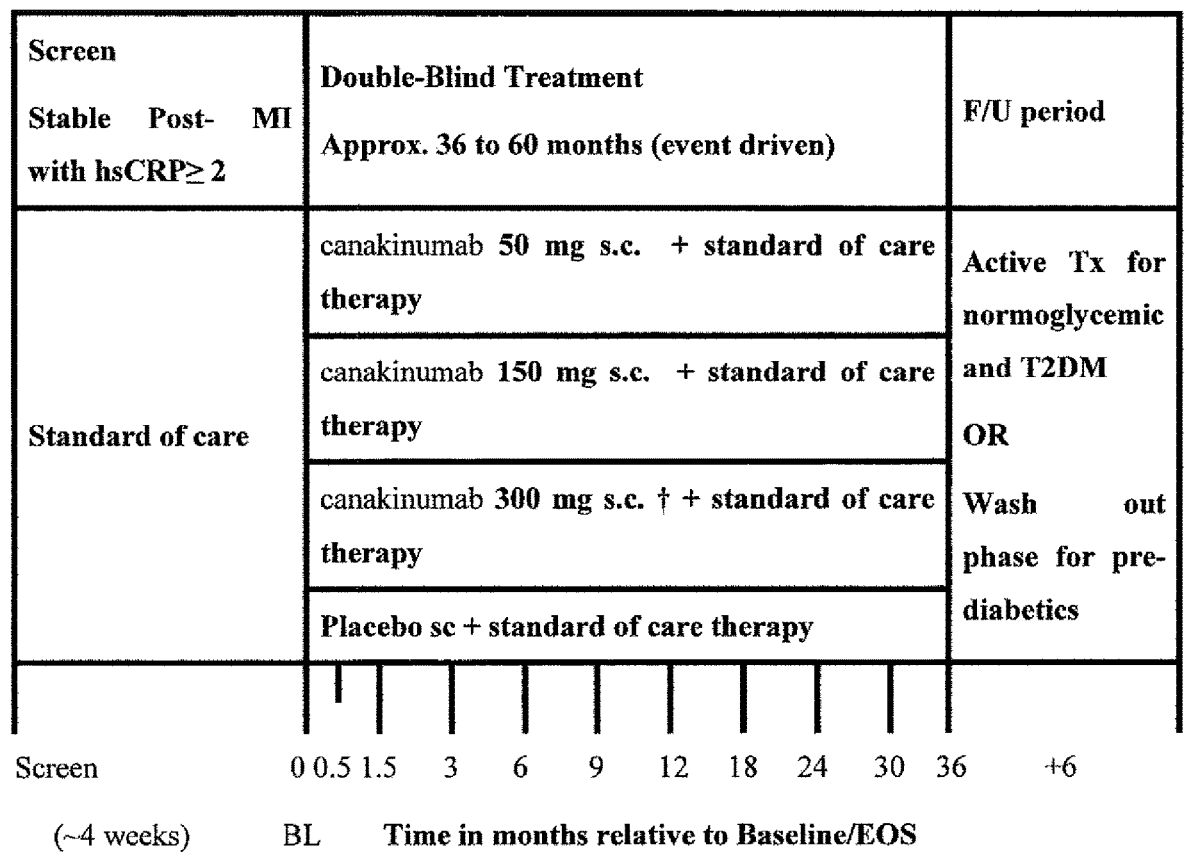

FIG. 9: The CACZ885M2301 study design. Months 15, 21, 27, 33 etc. are drug dispensing visits only and therefore not displayed. \-canakinumab 300 mg s.c. induction at randomization (month 0) and week 2 (month 0.5), and then 300 mg s.c. quarterly beginning at week 12.

DETAILED DESCRIPTION OF THE DISCLOSURE

The present invention provides, inter alia, methods of preventing or reducing risk of experiencing a recurrent cardiovascular (CV) event or a cerebrovascular event in a patient that has suffered of a qualifying CV event, comprising administering about 25 mg to about 300 mg of an IL-1β binding antibody or functional fragment thereof, wherein said patient has a CRP level of ≥about 1 mg/L before administration of said antibody or functional fragment thereof.

Canakinumab is a fully human monoclonal anti-human IL-1β antibody of the IgG1/k isotype, being developed for the treatment of IL-1β driven inflammatory diseases. It is designed to bind to human IL-1β and thus blocks the interaction of this cytokine with its receptors. The antagonism of the IL-1β mediated inflammation using canakinumab in lowering high sensitivity C-reactive protein (hsCRP) and other inflammatory marker levels has shown an acute phase response in patients with Cryopyrin-Associated Periodic Syndrome (CAPS) and rheumatoid arthritis. This evidence has been replicated in patients with type 2 diabetes mellitus (T2DM) using canakinumab and with other IL-1β antibody therapies in development.

Atherosclerotic vascular disease is the primary cause of morbidity and mortality in individuals with and without T2DM. The progression of atherosclerosis from endothelial dysfunction to vascular occlusion or to plaque rupture is the underlying mechanism responsible for many debilitating and life-threatening diseases such as MI, stroke and peripheral vascular disease (PVD). These diseases occur at higher frequency in T2DM patients and continue to increase despite use of current optimal therapies. There is also higher mortality rate after first MI in patients with T2DM compared to those without T2DM. Mortality associated with impaired glucose tolerance is 1.96 times higher compared to normal glucose tolerance. Thus, novel therapies that may improve vascular function, decrease atherosclerotic burden, and translate to a decrease in cardiovascular events would fill a significant unmet medical need.

T2DM is also a disease that is characterized by a high inflammatory state. Pre-clinical data suggests IL-1β is of key importance in the progressive functional impairment and destruction of β-cells in type 2 diabetes. Pancreatic β cells secrete IL-1β in response to elevated glucose exposure promoting further impairment of cellular viability via an autocrine action. IL-1β antagonism inhibits β cell death, promotes β cell proliferation, potentiates β cell glucose-induced insulin secretion and improves insulin sensitivity. Blocking IL-1β activity with an IL-1 receptor antagonist as well as a neutralizing IL-1β antibody in clinical trials reduced HbA1c Neutralization of IL-1β activity in the pancreatic islets is thus emerging as an attractive target for the treatment and prevention of type 2 diabetes. For T2DM prevention canakinumab's primary direct action is expected to prevent the IL-1β mediated destruction of pancreatic β-cells and thus prevent or delay progression of disease, which to date is a completely unmet need.

As demonstrated in a comprehensive 2010 meta-analysis of 54 prospective cohort studies, the inflammatory biomarker hsCRP is an independent risk factor for future cardiovascular events that (a) has a magnitude of effect similar to or larger than that of blood pressure or cholesterol and (b) has long-term stability and reproducibility at least as good as these widely-accepted risk factors (Kaptoge et al 2010). Abundant clinical trial data further demonstrate that persistent elevations of hsCRP are a major risk factor of recurrent vascular risk following myocardial infarction; for example, as demonstrated in the PROVE IT-TIMI 22 (Ridker et al 2005) and A-to-Z (Morrow et al 2006) trials. In both trials patients with known vascular disease and persistent elevation of hsCRP were at roughly double the risk for recurrent events compared to those with normal hsCRP levels. Further, stratification by hsCRP has proven highly effective in determining populations in who added cardiovascular benefits are observed with the use of efficacious lipid lowering agents, which also possess anti-inflammatory properties. This has been proven in primary prevention studies as including the AFCAPS/TexCAPS (Ridker et al 2001) and JUPITER trials (Ridker et al 2008, Ridker et al 2009) as well as in the setting of congestive heart failure (CHF) in the CORONA trial where efficacy of intervention was seen only among those with hsCRP ≥2 mg/L. Indeed, in this latter example, had stratification been done by hsCRP on an a priori basis, the trial would have been reported out as an overwhelming positive rather than as a null finding (McMurray et al 2009).

A direct anti-inflammatory agent could, in theory, be effective at any stage of the atherothrombotic process. However, the most appropriate population for a treatment with such an agent is one in which (a) patients are known to be at increased risk despite current therapy, and (b) there is biochemical evidence of a persistent heightened inflammatory response despite usual care. Recognizing these constraints, a primary prevention population would be infeasible due to the exceptionally large sample size required and because an extremely low side effect profile is typically required in that setting. In contrast, patients who have survived a MI are clinically stable, and who have persistently elevated hsCRP levels despite aggressive treatment are an optimal population in which to undertake a test of the inflammatory hypothesis of atherothrombosis. This population is no longer at risk for plaque rupture due to altered wound healing, yet remains at high risk for recurrent vascular events despite use of all accepted therapies.

Canakinumab and other IL-1 beta inhibiting agents, in particular other IL-1β binding antibodies, will reduce the risk of future occurrence of major cardiovascular events or cerebrovascular events in patients with recent past myocardial infarction (MI) by preventing IL-1β mediated vascular wall inflammation and endothelial dysfunction.

Canakinumab is disclosed in WO02/16436 which is hereby incorporated by reference in its entirety.

In one embodiment, the present disclosure provides a method of preventing or reducing risk of experiencing a recurrent cardiovascular (CV) event or a cerebrovascular event in a patient that has suffered of a qualifying CV event, comprising administering about 25 mg to about 300 mg of an IL-1β binding antibody or functional fragment thereof, wherein said patient has a CRP level of ≥about 1 mg/L before administration of said antibody or functional fragment thereof.

In one embodiment of any method of the invention, said CRP level is ≥about 2 mg/L. In one embodiment of any method of the invention said CRP level is ≥about 1, ≥about 1.1, ≥about 1.2, ≥about 1.3, ≥about 1.4. ≥about 1.5, ≥about 1.6, ≥about 1.7, ≥about 1.8, ≥about 1.9, ≥about 2.0, ≥about 2.1, ≥about 2.2, ≥about 2.3, ≥about 2.4, ≥about 2.5, ≥about 2.6, ≥about 2.7, ≥about 2.8, ≥about 2.9, ≥about 3.0 mg/L.

In some embodiment of any method of the invention said CRP level is 1-3 mg/L, or 1.5-2.5 mg/L, or 1.7-2.3 mg/L or 1.8-2.2 mg/L or 1.9-2.1 mg/L.

In one embodiment of any method of the invention, said level of CRP level is hsCRP level.

In one embodiment of any method of the invention, said IL-1β binding antibody or functional fragment thereof is administered 2-5 weeks from the qualifying CV event.

In other embodiments of any method of the invention, said IL-1β binding antibody or functional fragment thereof is administered 3 weeks or 21 days, 4 weeks or 1 month or 28 days, 5 weeks or 35 days, or 6 weeks or 42 days from the qualifying CV event.

In one embodiment of any method of the invention, said IL-1β binding antibody or functional fragment thereof is administered 3 years post a CABG (Coronary Artery Bypass Graft) procedure regardless of timing of a qualifying CV event.

In one embodiment of any method of the invention, said IL-1β binding antibody or functional fragment thereof is administered every 2 weeks, monthly, every 6 weeks, bimonthly (every 2 months), quarterly (every 3 months), every 5 months, or every 6 months from the first administration.

In one embodiment of any method of the invention, said recurrent CV event is selected from the group consisting of cardiovascular death, myocardial infarction (MI), or the cerebrovascular event is stroke.

In one embodiment of any method of the invention, said recurrent CV event is selected from the group consisting of acute coronary syndrome, hospitalization for unstable angina, other non-coronary ischemic event (transient ischemic attack or limb ischemia), any revascularization procedure (coronary and non-coronary), limb amputation, stent thrombosis (definite or probable), hospitalization or prolongation of hospitalization for heart failure, and coronary revascularization procedures (PCI or CABG).

In one embodiment, any method of the invention further comprises administering the patient an additional dose of about 25 mg to about 300 mg of the IL-1β binding antibody or functional fragment thereof at week 2, week 4 or week 6 from the first administration.

In one embodiment, the invention provides a method of preventing or reducing risk of experiencing a recurrent cardiovascular (CV) event or a cerebrovascular event in a patient that has suffered of a qualifying CV event, comprising administering about 50 mg of an IL-1β binding antibody or functional fragment thereof 2-5 weeks from the qualifying CV event, wherein said patient has a CRP level of ≥about 1 mg/L before administration of said antibody or functional fragment thereof, and further comprising administering the patient an additional dose of about 50 mg of the IL-1β binding antibody or functional fragment thereof at week 2, week 4 or week 6 from the first administration and followed by a quarterly administration from the first administration.

In one embodiment, the invention provides a method of preventing or reducing risk of experiencing a recurrent cardiovascular (CV) event or a cerebrovascular event in a patient that has suffered of a qualifying CV event, comprising administering about 150 mg of an IL-1β binding antibody or functional fragment thereof 2-5 weeks from the qualifying CV event, wherein said patient has a CRP level of ≥about 1 mg/L before administration of said antibody or functional fragment thereof, and further comprising administering the patient an additional dose of about 150 mg of the IL-1β binding antibody or functional fragment thereof at week 2, week 4 or week 6 from the first administration and followed by a quarterly administration from the first administration.

In one embodiment, the invention provides a method of preventing or reducing risk of experiencing a recurrent cardiovascular (CV) event or a cerebrovascular event in a patient that has suffered of a qualifying CV event, comprising administering about 300 mg of an IL-1β binding antibody or functional fragment thereof 2-5 weeks from the qualifying CV event, wherein said patient has a CRP level of ≥about 1 mg/L before administration of said antibody or functional fragment thereof and followed by a quarterly administration from the first administration.

In one embodiment, any method of the invention comprises administering about 25, 75, 100, 125, 175, 200, 225, 250, 275, 300 mg or any combination thereof of the IL-1β binding antibody or functional fragment thereof. In other embodiments of the administration regimens described above, a dose of about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 mg or any combination thereof of said IL-1β binding antibody or functional fragment thereof can be administered.

In one embodiment of any method of the invention, said IL-1β binding antibody or functional fragment thereof is an IL-1β binding antibody. In one embodiment of any method of the invention, said IL-1β binding antibody or functional fragment thereof is capable of inhibiting the binding of IL-1β to its receptor and has a $K_D$ for binding to IL-1β of about 50 pM or less.

In other embodiments of any method of the invention said IL-1β binding antibody is selected from the group consisting of:
 a) an IL-1β binding antibody directed to an antigenic epitope of human IL-1β which includes the loop comprising the Glu64 residue of the mature IL-1β, wherein said IL-1β binding antibody is capable of inhibiting the binding of IL-1β to its receptor, and further wherein said IL-1β binding antibody has a $K_D$ for binding to IL-1β of about 50 pM or less;
 b) an IL-1β binding antibody that competes with the binding of an IL-1β binding antibody comprising a VH domain comprising SEQ ID NO:1 and a VL domain comprising SEQ ID NO:2;
 c) an IL-1β binding antibody comprising the three CDRs of SEQ ID NO:3, SEQ ID NO:4, SEQ ID NO:5;
 d) an anti-IL-1β binding antibody comprising the three CDRs of SEQ ID NO:6, SEQ ID NO:7, SEQ ID NO:8;
 e) an anti-IL-1β binding antibody comprising the three CDRs of SEQ ID NO:3, SEQ ID NO:4, SEQ ID NO:5 and the three CDRs of SEQ ID NO:6, SEQ ID NO:7, SEQ ID NO:8;
 f) an anti-IL-1β binding antibody comprising a VH domain comprising SEQ ID NO:1;
 g) an anti-IL-1β binding antibody comprising a VL domain comprising SEQ ID NO:2;
 h) an anti-IL-1β binding antibody comprising a VH domain comprising SEQ ID NO:1 and a VL domain comprising SEQ ID NO:2.

In one embodiment of any method of the invention, said IL-1β binding antibody or fragment thereof comprises the 3

CDRs of SEQ ID NO:1 are set forth in SEQ ID NO:3, 4, and 5 and wherein the 3 CDRs of SEQ ID NO:2 are set forth in SEQ ID NO:6, 7, and 8.

In other embodiments of any method of the invention, the IL-1β binding antibody comprises:

a) a VH having a first CDR having 0, 1 or 2 amino acid substitutions in comparison to the CDR set forth in SEQ ID NO:3, a second CDR having 0, 1 or 2 amino acid substitutions in comparison to the CDR set forth in SEQ ID NO:3, a third CDR having 0, 1 or 2 amino acid substitutions in comparison to the CDR set forth in SEQ ID NO:5; and b) a VL having a first CDR having 0, 1 or 2 amino acid substitutions in comparison to the CDR set forth in SEQ ID NO:6, a second CDR having 0, 1 or 2 amino acid substitutions in comparison to the CDR set forth in SEQ ID NO:7, and a third CDR having 0, 1 or 2 amino acid substitutions in comparison to the CDR set forth in SEQ ID NO:8, wherein said antibody has a $K_D$ for IL-1beta of 50 pM or les and wherein said antibody inhibits the binding of IL-1β to its receptor.

Substituted amino acids are ideally conservative substitutions, and once substituted a skilled artisan could use an assay such as those described in WO02/16436.

In one embodiment of any method of the invention, said IL-1β binding antibody is canakinumab. In other embodiments of any method of the invention, said IL-1β binding antibody or functional fragment thereof is selected from the group consisting of XOMA 052 or gevokizumab, LY-2189102 or AMG-108.

In some embodiments of any of the method described above, the antibody or fragment binds to human IL-1β with a dissociation constant of about 50 pM or less. In some embodiments, the antibody or fragment binds to human IL-1β with a dissociation constant of about 500 pM or less. In some embodiments, the IL-1β binding antibody or functional fragment thereof binds to human IL-1β with a dissociation constant of about 250 pM or less. In some embodiments, the IL-1β binding antibody or functional fragment thereof binds to human IL-1β with a dissociation constant of about 100 pM or less. In some embodiments of any of the methods described above, the IL-1β binding antibody or functional fragment thereof binds to human IL-1β with a dissociation constant of about 5 pM or less. In some embodiments, the IL-1β binding antibody or functional fragment thereof binds to human IL-1β with a dissociation constant of about 1 pM or less. In some embodiments, the IL-1β binding antibody or functional fragment thereof binds to human IL-1β with dissociation constant of about 0.3 pM or less.

In some embodiments of any and/or all of the methods described above, the IL-1β binding antibody or functional fragment thereof is a neutralizing antibody.

The canakinumab heavy chain variable region (VH) is set forth as SEQ ID NO:1 of the sequence listing. CDR1 of the VH of canakinumab is set forth as SEQ ID NO:3 of the sequence listing. CDR2 of the VH of canakinumab is set forth as SEQ ID NO:4 of the sequence listing. CDR3 of the VH of canakinumab is set forth as SEQ ID NO:5 of the sequence listing.

The canakinumab light chain variable region (VL) is set forth as SEQ ID NO:2 of the sequence listing. CDR1 of the VL of canakinumab is set forth as SEQ ID NO:6 of the sequence listing. CDR2 of the VL of canakinumab is set forth as SEQ ID NO:7 of the sequence listing. CDR3 of the VL of canakinumab is set forth as SEQ ID NO:8 of the sequence listing.

In some embodiments of any and/or all of the methods described above, the anti-IL-1β binding antibody or binding fragment thereof competes with the binding of an antibody having the light chain variable region of SEQ ID NO:1 and the heavy chain variable region of SEQ ID NO:2.

FIG. 7 illustrates the sequence of VH and of the three CDRs

In some embodiments, the disclosed methods comprise administering an anti-IL-1β binding antibody having the three CDRs of SEQ ID NO:1. In further embodiments, the three CDRs of SEQ ID NO:1 are set forth as SEQ ID NOs:3-5. In some embodiments, the disclosed methods comprise administering an anti-IL-1β binding antibody having the three CDRs of SEQ ID NO:2. In further embodiments, the three CDRs of SEQ ID NO:2 are set forth as SEQ ID NOs:6-8.

FIG. 8 illustrates the sequence of VL and of the three CDRs.

In some embodiments, the disclosed methods comprise administering an anti-IL-1β binding antibody having the three CDRs of SEQ ID NO:1 and the three CDRs of SEQ ID NO:2. In further embodiments, the three CDRs of SEQ ID NO:1 are set forth as SEQ ID NOs:3-5 and the three CDRs of SEQ ID NO:2 are set forth as SEQ ID NOs:6-8.

In some embodiments of any of the method described above, said IL-1β binding antibody or functional fragment thereof is administered subcutaneously or intravenously.

When administered subcutaneously, canakinumab can be administered in a reconstituted formulation comprising canakinumab at concentration 10-150 mg/ml, 270 mM sucrose, 30 mM histidine and 0.06% polysorbate 80, wherein the pH of the formulation is 6.3-6.7, preferably 6.5.

When administered subcutaneously, canakinumab can be administered in a liquid formulation comprising canakinumab at concentration: 10-150 mg/ml, 270 mM mannitol, 20 mM histidine and 0.04% polysorbate 80 (or polysorbate 20), wherein the pH of the formulation is 6.3-6.7, preferably 6.5.

When administered subcutaneously, canakinumab or any of said IL-1β binding antibody or functional fragment thereof can be administered to the patient in a liquid form or lyophilized form for reconstitution contained in a prefilled syringe.

In other embodiments, any method of the invention, comprises assessing patient reported outcomes which include tiredness, physical function and performance function, comprising tiredness, physical function and performance function, whereby said patient reported outcomes (PRO) are improved by said method.

In other embodiments of any method of the invention, said patient is concomitantly receiving standard of care treatment for preventing or reducing risk of experiencing recurrent CV events. Said standard of care treatment is a lipid lowering agent such as a HMG-CoA reductase inhibitor, e.g., a statin such as lovastatin, pravastatin, simvastatin, fluvastatin, atorvastatin, cerivastatin, mevastatin, pitavastatin, rosuvastatin or mixtures thereof or mixtures with ezetimibe, niacin, amlodipine besylate), anti-hypertensives such as a calcium channel blocker (e.g., amlodipine, diltiazem, nifedipine, nicardipine, verapamil) or beta-adrenergic blocking drugs such as esmolol, metoprolol, nadolol, penbutolol or anti-hypertensives such as labetalol, metoprolol, hydralazine, nitroglycerin, nicardipine, sodium nitroprusside, clevidipine or a diuretic such as a thiazide diuretic, chlorthalidone, furosemide, hydrochlorothiazide, indapamide, metolazone, amiloride hydrochloride, spironolactone, triamterene, or an angiotensin-converting enzyme (ACE) inhibitor such as ramipril, ramiprilat, captopril, lisinopril or an angiotensin II receptor blocker such as losartan, valsartan, olmesartan, irbesartan, candesartan, telmisartan, eprosartan or an anticoagulant such as acenocoumarol, coumatetralyl, dicoumarol, ethyl biscoumacetate, phenprocoumon, warfarin heparin, low molecular weight heparin such as bemiparin, certoparin, dalteparin, enoxaparin, nadroparin, parnaparin, reviparin, tinzaparin or an inhibitor of platelet aggregation such clopidogrel, elinogrel, prasugrel, cangrelor, ticagrelor, ticlopidine, cilostazol, dipyridamole, picodamide eptifibatide, abciximab, eptifibatide, tirofiban or terutroban or a Prostaglandin analogue (PGI2) such as beraprost, prostacyclin, iloprost or treprostinil, or COX inhibitors such as aspirin, aloxiprin or carbasalate calcium, indobufen or triflusal or cloricromen or ditazole or 1,3-Indandiones such as clorindione, diphenadione or phenindion, or tioclomarol, or direct thrombin (II) inhibitors such as hirudin, bivalirudin, lepirudin, desirudin (bivalent) or argatroban or dabigatran (monovalent) or oligosaccharides such as fondaparinux, idraparinux, or an heparinoids such as danaparoid, sulodexide, dermatan sulfate or direct Xa inhibitors xabans such as apixaban, betrixaban, edoxaban, otamixaban, rivaroxaban or REG1 or defibrotide or ramatroban or antithrombin III or protein C (drotrecogin alfa) or fibrinolytics plasminogen activators: r-tPA such as alteplase, reteplase, tenecteplase or UPA such as urokinase or saruplase) or streptokinase or anistreplase or monteplase or other serine endopeptidases or ancrod or fibrinolysin; or brinase or citrate or EDTA or oxalate or digitalis, or digoxin, or nesiritide, or oxygen, or a nitrate such as glyceryl trinitrate (GTN)/nitroglycerin, isosorbide dinitrate, isosorbide mononitrate or an analgesic such as morphine sulfate or a renin inhibitor such as aliskiren or an endothelin A receptor inhibitor or an aldosterone inhibitor.

In other embodiments of any method according to the invention, biomarkers other than hsCRP include but are not limited to: IL-1Ra, IL-6, IL-18, leptin, adiponectin (total and high MW), TNFα, PAI-1 and fibrinogen.

In a particularly preferred embodiment, said IL-1β binding antibody is canakinumab.

In other embodiments, said IL-1β binding antibody is XOMA 052 or gevokizumab, LY-2189102 or AMG-108.

Other embodiments of the invention include:

An IL-1β binding antibody or a functional fragment thereof for use in preventing or reducing risk of experiencing a recurrent cardiovascular (CV) event or a cerebrovascular event in a patient that has suffered of a qualifying CV event, wherein i) about 25 mg to about 300 mg of said IL-1β binding antibody or functional fragment thereof is to be administered, and wherein ii) said patient has a CRP level of ≥about 1 mg/L before administration of said antibody or functional fragment thereof.

Other embodiments of the invention include the use of an IL-1β binding antibody for the manufacture of a medicament according to any of the described uses or methods herein.

In another embodiment the use of an IL-1β binding antibody is provided for the manufacture of a medicament for preventing or reducing risk of experiencing a recurrent cardiovascular (CV) event or a cerebrovascular event in a patient that has suffered of a qualifying CV event, wherein i) about 25 mg to about 300 mg of said IL-1β binding antibody or functional fragment thereof is to be administered, and wherein ii) said patient has a CRP level of ≥about 1 mg/L before administration of said antibody or functional fragment thereof.

In one embodiment of any use of the invention, said CRP level is ≥about 2 mg/L. In one embodiment of any use of the invention said CRP level is ≥about 1, ≥about 1.1, ≥about 1.2, ≥about 1.3, ≥about 1.4. ≥about 1.5, ≥about 1.6, ≥about 1.7, ≥about 1.8, ≥about 1.9, ≥about 2.0, ≥about 2.1, ≥about 2.2, ≥about 2.3, ≥about 2.4, ≥about 2.5, ≥about 2.6, ≥about 2.7, ≥about 2.8. ≥about 2.9, ≥about 3.0 mg/L. In some embodiment of any use of the invention said CRP level is 1-3 mg/L, or 1.5-2.5 mg/L, or 1.7-2.3 mg/L or 1.8-2.2 mg/L or 1.9-2.1 mg/L.

In one embodiment of any use of the invention, said level of CRP level is hsCRP level.

In one embodiment of any use of the invention, said IL-1β binding antibody or functional fragment thereof is to be administered 2-5 weeks from the qualifying CV event.

In other embodiments of any use of the invention, said IL-1β binding antibody or functional fragment thereof is to be administered 3 weeks or 21 days, 4 weeks or 1 month or 28 days, 5 weeks or 35 days, or 6 weeks or 42 days from the qualifying CV event.

In one embodiment of any use of the invention, said IL-1β binding antibody or functional fragment thereof is to be administered 3 years post a CABG (Coronary Artery Bypass Graft) procedure regardless of timing of a qualifying CV event.

In one embodiment of any use of the invention, said IL-1β binding antibody or functional fragment thereof is to be administered every 2 weeks, monthly, every 6 weeks, bimonthly (every 2 months), quarterly (every 3 months), every 5 months, or every 6 months from the first administration.

In one embodiment of any use of the invention, said recurrent CV event is selected from the group consisting of cardiovascular death, myocardial infarction (MI), and the cerebrovascular event can be stroke.

In one embodiment of any use of the invention, said recurrent CV event is selected from the group consisting of hospitalization for unstable angina, other non-coronary ischemic event (transient ischemic attack or limb ischemia), any revascularization procedure (coronary and non-coronary), limb amputation, stent thrombosis (definite or probable), hospitalization or prolongation of hospitalization for heart failure, and coronary revascularization procedures (PCI or CABG).

In one embodiment of any use of the invention, said patient is to be administered an additional dose of about 25 mg to about 300 mg of the IL-1β binding antibody or functional fragment thereof at week 2, week 4 or week 6 from the first administration.

In one embodiment, the invention provides an IL-1β binding antibody or functional fragment thereof for use in preventing or reducing risk of experiencing a recurrent cardiovascular (CV) event or a cerebrovascular event in a patient that has suffered of a qualifying CV event, wherein i) said patient has a CRP level of ≥about 1 mg/L before administration of said antibody or functional fragment thereof, and wherein ii) about 50 mg of said IL-1β binding antibody or functional fragment thereof is to be administered 2-5 weeks from the qualifying CV event, and wherein iii) an additional dose of about 50 mg of the IL-1β binding antibody or functional fragment thereof is to be administered at week 2, week 4 or week 6 from the first administration, and wherein iv) about 50 mg of said IL-1β binding antibody or functional fragment thereof is to be quarterly (every 3 months) from the first administration.

In one embodiment, the invention provides an IL-1β binding antibody or functional fragment thereof for use in of preventing or reducing risk of experiencing a recurrent cardiovascular (CV) event or a cerebrovascular event in a patient that has suffered of a qualifying CV event, wherein
  i) said patient has a CRP level of ≥about 1 mg/L before administration of said antibody or functional fragment thereof, and wherein
  ii) about 150 mg of said IL-1β binding antibody or functional fragment thereof is to be administered 2-5 weeks from the qualifying CV event, and wherein
  iii) an additional dose of about 150 mg of the IL-1β binding antibody or functional fragment thereof is to be administered at week 2, week 4 or week 6 from the first administration.

In one embodiment, the invention provides an IL-1β binding antibody or functional fragment thereof for use in preventing or reducing risk of experiencing a recurrent cardiovascular (CV) event or a cerebrovascular event in a patient that has suffered of a qualifying CV event, wherein
  i) said patient has a CRP level of ≥about 1 mg/L before administration of said antibody or functional fragment thereof, and wherein
  ii) about 50 mg of said IL-1β binding antibody or functional fragment thereof is to be administered 2-5 weeks from the qualifying CV event, and wherein
  iii) an additional dose of about 50 mg of the IL-1β binding antibody or functional fragment thereof is to be administered at week 2, week 4 or week 6 from the first administration.

In one embodiment, any use of the invention, said patient is to be administered about 25, 75, 100, 125, 175, 200, 225, 250, 275, 300 mg or any combination thereof of the IL-1β binding antibody or functional fragment thereof. In other embodiments of the uses described above, said patient is to be administered about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 mg or any combination thereof of said IL-1β binding antibody or functional fragment thereof.

In one embodiment of any use of the invention, said IL-1β binding antibody or functional fragment thereof is an IL-1β binding antibody. In one embodiment of any use of the invention, said IL-1β binding antibody or functional fragment thereof is capable of inhibiting the binding of IL-1β to its receptor and has a $K_D$ for binding to IL-1β of about 50 pM or less.

In other embodiments of any use of the invention said IL-1β binding antibody is selected from the group consisting of:
  a) an IL-1β binding antibody directed ton antigenic epitope of human IL-1β which includes the loop comprising the Glu64 residue of the mature IL-1β, wherein said IL-1β binding antibody is capable of inhibiting the binding of IL-1β to its receptor, and further wherein said IL-1β binding antibody has a $K_D$ for binding to IL-1β of about 50 pM or less;
  b) an IL-1β binding antibody that competes with the binding of an IL-1β binding antibody comprising a VH domain comprising SEQ ID NO:1 and a VL domain comprising SEQ ID NO:2;
  c) an anti-IL-1β binding antibody comprising the three CDRs of SEQ ID NO:3, SEQ ID NO:4, SEQ ID NO:5;
  d) an anti-IL-1β binding antibody comprising the three CDRs of SEQ ID NO:6, SEQ ID NO:7, SEQ ID NO:8;
  e) an anti-IL-1β binding antibody comprising the three CDRs of SEQ ID NO:3, SEQ ID NO:4, SEQ ID NO:5 and the three CDRs of SEQ ID NO:6, SEQ ID NO:7, SEQ ID NO:8;
  f) an anti-IL-1β binding antibody comprising a VH domain comprising SEQ ID NO:1;
  g) an anti-IL-1β binding antibody comprising a VL domain comprising SEQ ID NO:2;
  h) an anti-IL-1β binding antibody comprising a VH domain comprising SEQ ID NO:1 and a VL domain comprising SEQ ID NO:2.

In one embodiment of any use of the invention, said IL-1β binding antibody or fragment thereof comprises the 3 CDRs of SEQ ID NO:1 are set forth in SEQ ID NO:3, 4, and 5 and comprises the 3 CDRs of SEQ ID NO:2 are set forth in SEQ ID NO:6, 7, and 8.

In other embodiments of any use of the invention, said IL-1β binding antibody or functional fragment thereof comprises:
  a) a VH having a first CDR having 0, 1 or 2 amino acid substitutions in comparison to the CDR set forth in SEQ ID NO:3, a second CDR having 0, 1 or 2 amino acid substitutions in comparison to the CDR set forth in SEQ ID NO:3, a third CDR having 0, 1 or 2 amino acid substitutions in comparison to the CDR set forth in SEQ ID NO:5; and
  b) a VL having a first CDR having 0, 1 or 2 amino acid substitutions in comparison to the CDR set forth in SEQ ID NO:6, a second CDR having 0, 1 or 2 amino acid substitutions in comparison to the CDR set forth in SEQ ID NO:7, and a third CDR having 0, 1 or 2 amino acid substitutions in comparison to the CDR set forth in SEQ ID NO:8, wherein said antibody has a $K_D$ for IL-1beta of 50 pM or les and wherein said antibody inhibits the binding of IL-1β to its receptor.

Substituted amino acids are ideally conservative substitutions, and once substituted a skilled artisan could use an assay such as those described in WO02/16436.

In one embodiment of any use of the invention, said IL-1β binding antibody is canakinumab. In other embodiments of any use of the invention, said IL-1β binding antibody or functional fragment thereof is selected from the group consisting of XOMA 052 or gevokizumab (as disclosed in WO2007/002261, incorporated by reference in its entirety), LY-2189102 or AMG-108.

In some embodiments of any of the use described above, said IL-1β binding antibody or functional fragment thereof binds to human IL-1β with a dissociation constant of about 50 pM or less. In some embodiments, the antibody or fragment binds to human IL-1β with a dissociation constant of about 500 pM or less. In some embodiments, the IL-1β binding antibody or functional fragment thereof binds to human IL-1β with a dissociation constant of about 250 pM or less. In some embodiments, the IL-1β binding antibody or functional fragment thereof binds to human IL-1β with a dissociation constant of about 100 pM or less. In some embodiments of any of the uses described above, the IL-1β binding antibody or functional fragment thereof binds to human IL-1β with a dissociation constant of about 5 pM or less. In some embodiments, the IL-1β binding antibody or functional fragment thereof binds to human IL-1β with a dissociation constant of about 1 pM or less. In some embodiments, the IL-1β binding antibody or functional fragment thereof binds to human IL-1β with dissociation constant of about 0.3 pM or less.

In some embodiments of any of the uses described above, the IL-1β binding antibody or fragment thereof is a neutralizing antibody.

The canakinumab heavy chain variable region (VH) is set forth as SEQ ID NO:1 of the sequence listing. CDR1 of the VH of canakinumab is set forth as SEQ ID NO:3 of the sequence listing. CDR2 of the VH of canakinumab is set forth as SEQ ID NO:4 of the sequence listing. CDR3 of the VH of canakinumab is set forth as SEQ ID NO:5 of the sequence listing.

The canakinumab light chain variable region (VL) is set forth as SEQ ID NO:2 of the sequence listing. CDR1 of the VL of canakinumab is set forth as SEQ ID NO:6 of the sequence listing. CDR2 of the VL of canakinumab is set forth as SEQ ID NO:7 of the sequence listing. CDR3 of the VL of canakinumab is set forth as SEQ ID NO:8 of the sequence listing.

In some embodiments of any of the uses described above, the IL-1β binding antibody or fragment thereof competes with the binding of an antibody having the light chain variable region of SEQ ID NO:1 and the heavy chain variable region of SEQ ID NO:2.

FIG. 7 illustrates the sequence of VH and of the three CDRs.

In some embodiments, the disclosed uses, said IL-1β binding antibody having the three CDRs of SEQ ID NO:1. In further embodiments, the three CDRs of SEQ ID NO:1 are set forth as SEQ ID NOs:3-5. In some embodiments, the disclosed uses comprise administering an anti-IL-1β binding antibody having the three CDRs of SEQ ID NO:2. In further embodiments, the three CDRs of SEQ ID NO:2 are set forth as SEQ ID NOs:6-8.

FIG. 8 illustrates the sequence of VL and of the three CDRs.

In some embodiments, the disclosed uses comprise administering an anti-IL-1β binding antibody having the three CDRs of SEQ ID NO:1 and the three CDRs of SEQ ID NO:2. In further embodiments, the three CDRs of SEQ ID NO:1 are set forth as SEQ ID NOs:3-5 and the three CDRs of SEQ ID NO:2 are set forth as SEQ ID NOs:6-8.

In some embodiments of any of the use described above, said IL-1β binding antibody or functional fragment thereof is to be administered subcutaneously or intravenously.

When administered subcutaneously, canakinumab can be administered in a reconstituted formulation comprising canakinumab at concentration 10-150 mg/ml, 270 mM sucrose, 30 mM histidine and 0.06% polysorbate 80, wherein the pH of the formulation is 6.3-6.7, preferably 6.5.

When administered subcutaneously, canakinumab can be administered in a liquid formulation comprising canakinumab at concentration: 10-150 mg/ml, 270 mM mannitol, 20 mM histidine and 0.04% polysorbate 80 (or polysorbate 20), wherein the pH of the formulation is 6.3-6.7, preferably 6.5.

When administered subcutaneously, canakinumab or any of said IL-1β binding antibody or functional fragment thereof can be administered to the patient in a liquid form or lyophilized form for reconstitution contained in a prefilled syringe. In one embodiment said prefilled syringe can be contained in an autoinjector. Such autoinjector makes it possible for the patient to selfadminister the liquid formulation subcutanously in an easy manner.

In other embodiments according to any use of the invention, patient reported outcomes which include tiredness, physical function and performance function are assessed, and whereby said patient reported outcomes (PRO) are improved.

In other embodiments of any use of the invention, said patient is concomitantly receiving standard of care treatment for preventing or reducing risk of experiencing recurrent CV events. Said standard of care treatment is a lipid lowering agent such as a HMG-CoA reductase inhibitor, e.g., a statin such as lovastatin, pravastatin, simvastatin, fluvastatin, atorvastatin, cerivastatin, mevastatin, pitavastatin, rosuvastatin or mixtures thereof or mixtures with ezetimibe, niacin, amlodipine besylate), anti-hypertensives such as a calcium channel blocker (e.g., amlodipine, diltiazem, nifedipine, nicardipine, verapamil) or beta-adrenergic blocking drugs such as esmolol, metoprolol, nadolol, penbutolol or antihypertensives such as labetalol, metoprolol, hydralazine, nitroglycerin, nicardipine, sodium nitroprusside, clevidipine or a diuretic such as a thiazide diuretic, chlorthalidone, furosemide, hydrochlorothiazide, indapamide, metolazone, amiloride hydrochloride, spironolactone, triamterene, or an angiotensin-converting enzyme (ACE) inhibitor such as ramipril, ramiprilat, captopril, lisinopril or an angiotensin II receptor blocker such as losartan, valsartan, olmesartan, irbesartan, candesartan, telmisartan, eprosartan or an anticoagulant such as acenocoumarol, coumatetralyl, dicoumarol, ethyl biscoumacetate, phenprocoumon, warfarin heparin, low molecular weight heparin such as bemiparin, certoparin, dalteparin, enoxaparin, nadroparin, parnaparin, reviparin, tinzaparin or an inhibitor of platelet aggregation such clopidogrel, elinogrel, prasugrel, cangrelor, ticagrelor, ticlopidine, cilostazol, dipyridamole, picodamide eptifibatide, abciximab, eptifibatide, tirofiban or terutroban or a Prostaglandin analogue (PGI2) such as beraprost, prostacyclin, iloprost or treprostinil, or COX inhibitors such as aspirin, aloxiprin or carbasalate calcium, indobufen or triflusal or cloricromen or ditazole or 1,3-Indandiones such as clorindione, diphenadione or phenindion, or tioclomarol, or direct thrombin (II) inhibitors such as hirudin, bivalirudin, lepirudin, desirudin (bivalent) or argatroban or dabigatran (monovalent) or oligosaccharides such as fondaparinux, idraparinux, or an heparinoids such as danaparoid, sulodexide, dermatan sulfate or direct Xa inhibitors xabans such as apixaban, betrixaban, edoxaban, otamixaban, rivaroxaban or REG1 or defibrotide or ramatroban or antithrombin III or protein C (drotrecogin alfa) or fibrinolytics plasminogen activators: r-tPA such as alteplase, reteplase, tenecteplase or UPA such as urokinase or saruplase) or streptokinase or anistreplase or monteplase or other serine endopeptidases or ancrod or fibrinolysin; or brinase or citrate or EDTA or oxalate or digitalis, or digoxin, or nesiritide, or oxygen, or a nitrate such as glyceryl trinitrate (GTN)/nitroglycerin, isosorbide dinitrate, isosorbide mononitrate or an analgesic such as morphine sulfate or a renin inhibitor such as aliskiren or an endothelin A receptor inhibitor or an aldosterone inhibitor.

In other embodiments of any use according to the invention, biomarkers other than hsCRP include but are not limited to: IL-1Ra, IL-6, IL-18, leptin, adiponectin (total and high MW), TNFα, PAI-1 and fibrinogen.

Other embodiments of any aspect described above include a pharmaceutical composition for preventing or reducing risk of experiencing a recurrent cardiovascular (CV) event a cerebrovascular event in a patient that has suffered of a qualifying CV event, wherein about 25 mg to about 300 mg of an IL-1β binding antibody or functional fragment thereof is to be administered, and wherein said patient has a CRP level of ≥about 1 mg/L before administration of said antibody or functional fragment thereof.

General:

All patents, published patent applications, publications, references and other material referred to herein are incorporated by reference herein in their entirety.

As used herein, the term "comprising" encompasses "including" as well as "consisting," e.g. a composition "comprising" X may consist exclusively of X or may include something additional, e.g., X+Y.

As used herein, the term "administering" in relation to a compound, e.g., an IL-1β binding antibody or standard of care agent, is used to refer to delivery of that compound by any route of delivery.

As used herein, the term "assaying" is used to refer to the act of detecting, identifying, screening, or determining, which act may be performed by any conventional means. For example, a sample may be assayed for the presence of a particular marker by using an ELISA assay, a Northern blot, imaging, etc. to detect whether that marker is present in the sample.

As used herein, The term "about" in relation to a numerical value x means, for example, +/−10%.

As used herein, The word "substantially" does not exclude "completely," e.g., a composition which is "substantially free" from Y may be completely free from Y. Where necessary, the word "substantially" may be omitted from the definition of the disclosure.

As used herein, "C-reactive protein" and "CRP" refers to serum C-reactive protein, which is used as an indicator of the acute phase response to inflammation. The level of CRP in plasma may be given in any concentration, e.g., mg/dl, mg/L, nmol/L. Levels of CRP may be measured by a variety of well known methods, e.g., radial immunodiffusion, electroimmunoassay, immunoturbidimetry, ELISA, turbidimetric methods, fluorescence polarization immunoassay, and laser nephelometry.

Testing for CRP may employ a standard CRP test or a high sensitivity CRP (hsCRP) test (i.e., a high sensitivity test that is capable of measuring low levels of CRP in a sample using laser nephelometry). Kits for detecting levels of CRP may be purchased from various companies, e.g., Calbiotech, Inc, Cayman Chemical, Roche Diagnostics Corporation, Abazyme, DADE Behring, Abnova Corporation, Aniara Corporation, Bio-Quant Inc., Siemens Healthcare Diagnostics, etc.

As used herein, the term "hsCRP" refers to the level of CRP in the blood as measured by high sensitivity CRP testing.

Each local laboratory will employ a cutoff value for abnormal (high) CRP based on that laboratory's rule for calculating normal maximum CRP. A physician generally orders a CRP test from a local laboratory, and the local laboratory reports normal or abnormal (low or high) CRP using the rule that particular laboratory employs to calculate normal CRP.

By "IL-1β binding antibody" is meant any antibody capable of binding to the IL-1β antigen either alone or associated with other molecules. The binding reaction may be shown by standard methods (qualitative assays) including, for example, a bioassay for determining the inhibition of IL-1β binding to its receptor or any kind of binding assays, with reference to a negative control test in which an antibody of unrelated specificity but of the same isotype, e.g. an anti-CD25 antibody, is used. Advantageously, the binding of the IL-1β binding antibodies used in the methods of the invention to IL-1β may be shown in a competitive binding assay.

As used herein the term "antibody" as referred to herein includes whole antibodies and any antigen binding fragment or single chains thereof (i.e., "functional fragment"). A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

As used herein, the term "functional fragment" of an antibody as used herein, refers to portions or fragments of an antibody that retain the ability to specifically bind to an antigen (e.g., IL-1β). It has been shown that the antigen-binding function of an antibody can be performed by fragments of a full-length antibody. Examples of binding fragments encompassed within the term "functional fragment" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989), which consists of a $V_H$ domain; and an isolated complementarity determining region (CDR). Exemplary antigen binding sites include the CDRs of canakinumab as set forth in SEQ ID NOs: 3-5 and SEQ ID NOs: 6-8. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988; and Huston et al., 1988). Such single chain antibodies are also intended to be encompassed within the term "functional fragments" of an antibody. These antibody fragments are obtained using conventional techniques known to those of skill in the art, and the fragments are screened for utility in the same manner as are intact antibodies.

As used herein, the terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "human antibody", as used herein, is intended to include antibodies having variable regions in which both the framework and CDR regions are derived from sequences of human origin. Furthermore, if the antibody contains a constant region, the constant region also is derived from such human sequences, e.g., human germ-line sequences, or mutated versions of human germline sequences or antibody containing consensus framework sequences derived from human framework sequences analysis as described in Knappik, et al. A "human antibody" need not be produced by a human, human tissue or human cell.

The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, the term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "patient" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

As used herein, an antibody that "inhibits" one or more of these IL-1β functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-1β activity affects a statistically significant decrease, e.g., by at least 10% of the measured parameter, by at least 50%, 80% or 90%, and in certain embodiments an antibody of the disclosure may inhibit greater than 95%, 98% or 99% of IL-17 functional activity.

As used herein the term "polypeptide", if not otherwise specified herein, includes any peptide or protein comprising amino acids joined to each other by peptide bonds, having an amino acid sequence starting at the N-terminal extremity and ending at the C-terminal extremity.

As used herein, the term "qualifying CV event" is MI, stroke, unstable angina, revascularization, stent thrombosis, acute coronary syndrome or any other CV event (excluding cardiovascular death) which precedes the start of IL-1β binding antibody or functional fragment thereof therapy. In particular MI is a preferred qualifying CV event.

As used herein, the term "recurrent CV event" is a repeated CV event including but not limited to CV death, MI, or acute coronary syndrome which takes place after said qualifying CV event.

As used herein "cerebrovascular disease" is a group of brain dysfunctions related to disease of the blood vessels supplying the brain. This definition includes but are not limited to stroke.

As used herein, the term "cardiovascular death" includes sudden cardiac death, death due to acute myocardial infarction, death due to heart failure, death due to stroke, and death due to other cardiovascular causes.

As used herein, "sudden cardiac death" is a sudden death that occurs in a previously stable patient who does not have a prior terminal condition, such as malignancy not in remission or end-stage chronic lung disease.

Death due to acute myocardial infarction (AMI): refers to a death within 30 days after a myocardial infarction (MI) related to consequences seen immediately after the myocardial infarction, such as progressive congestive heart failure (CHF), inadequate cardiac output, or recalcitrant arrhythmia. If these events occur after a "break" (e.g., a CHF and arrhythmia free period), they should be designated by the immediate cause. The acute myocardial infarction should be verified either by the diagnostic criteria outlined for acute myocardial infarction or by autopsy findings showing recent myocardial infarction or recent coronary thrombus, and there should be no conclusive evidence of another cause of death.

Sudden, unexpected cardiac death, involving cardiac arrest, often with symptoms suggestive of myocardial ischemia, and accompanied by presumably new ST elevation, or new LBBB and/or evidence of fresh thrombus by coronary angiography and/or at autopsy, but death occurring before blood samples could be obtained, or at a time before the appearance of cardiac biomarkers in the blood should be considered death due to acute myocardial infarction.

If death occurs before biochemical confirmation of myocardial necrosis can be obtained, adjudication should be based on clinical presentation and ECG evidence.

Death resulting from a procedure to treat myocardial ischemia or to treat a complication resulting from myocardial infarction should also be considered death due to acute MI.

Death due to a myocardial infarction that occurs as a direct consequence of a cardiovascular investigation/procedure/operation should be classified as death due to other cardiovascular cause.

Death due to heart failure or cardiogenic shock refers to death occurring in the context of clinically worsening symptoms and/or signs of heart without evidence of another cause of death.

Death due to heart failure or cardiogenic shock should include sudden death occurring during an admission for worsening heart failure as well as death from progressive heart failure or cardiogenic shock following implantation of a mechanical assist device.

Death due to stroke (intracranial hemorrhage or non-hemorrhagic stroke) refers to death occurring up to 30 days after a suspected stroke based on clinical signs and symptoms as well as neuroimaging and/or autopsy, and where there is no conclusive evidence of another cause of death.

As used herein, "death due to other cardiovascular causes" refers to death due to a cardiovascular cause not included in the above categories (e.g. dysrhythmia, pulmonary embolism, cardiovascular intervention, aortic aneurysm rupture, or peripheral arterial disease). Mortal complications of cardiac surgery or non-surgical revascularization, even if "non-cardiovascular" in nature, should be classified as cardiovascular deaths.

As used herein the term "death of undetermined cause" (presumed cardiovascular) refers to all deaths not attributed to the categories of cardiovascular Death or to a non-cardiovascular cause are considered presumed cardiovascular deaths. As used herein, "non-cardiovascular death" is defined as any death not covered by cardiac death or vascular death and is categorized as follows: pulmonary causes, renal causes, gastrointestinal causes, infection (including sepsis), non-infectious causes, malignancy, accident/Trauma, suicide, non-cardiovascular system organ failure (e.g. hepatic), hemorrhage, not intracranial or other.

As used herein, the term "myocardial infarction (MI)" refers to "acute Myocardial Infarction": the term myocardial infarction (MI) should be used when there is evidence of myocardial necrosis in a clinical setting consistent with myocardial ischemia. Under these conditions any one of the following criteria meets the diagnosis for MI.

The term "spontaneous MI" refers to the detection of rise and/or fall of cardiac biomarkers with at least one value above the 99th percentile of the upper reference limit (URL) together with evidence of myocardial ischemia with at least one of the following: symptoms of ischemia, ECG changes indicative of new ischemia), development of pathological Q waves in the ECG, imaging evidence of new loss of viable myocardium or new regional wall motion abnormality.

The term "percutaneous coronary intervention (PCI) related myocardial infarct" refers to PCI in patients with normal baseline troponin values elevations of cardiac biomarkers above the 99th percentile URL within 24 hours of the procedure are indicative of peri-procedural myocardial necrosis. By convention increases of biomarkers greater than $3 \times 99^{th}$ percentile URL are consistent with PCI related myocardial infarction. If the cardiac biomarker is elevated prior to PCI a ≥20% increase of the value in that second cardiac biomarker within 24 hours of the PCI and documentation that cardiac biomarkers were decreasing (two samples at least 6 hours apart) prior to the suspected recurrent MI is also consistent with PCI related MI. Symptoms of cardiac ischemia are not required The term "CABG related myocardial infarct" refers to CABG in patients with normal baseline troponin, elevations of cardiac biomarkers above 5 times the $99^{th}$ percentile of the normal reference range during the first 72 hours after CABG, when associated with either new pathological Q waves in at least 2 contiguous leads on the ECG that persist through 30 days or new left bundle branch block (LBBB) or angiographically documented new graft or native coronary artery occlusion or imaging evidence of new loss of viable myocardium If the cardiac biomarker is elevated prior to CABG a ≥20% increase of the value in the second cardiac biomarker within 72 hours of CABG AND documentation that the cardiac biomarkers were decreasing (2 samples at least 6 hours apart) prior to the suspected recurrent MI plus either new pathological Q waves in at least 2 contiguous leads on the ECG or new LBBB, angiographically documented new graft or native artery occlusion or imaging evidence or new loss of viable myocardium is consistent with a peri-procedural myocardial infarct after CABG. Symptoms of cardiac ischemia are not required.

Criteria for Prior Myocardial Infarction: Any of the following criteria meets the diagnosis for prior myocardial infarction: development of new pathological Q waves with or without symptoms, imaging evidence of a region of loss of viable myocardium that is thinned and fails to contract in the absence of a non-ischemic cause, pathological findings of a healed or healing myocardial infarction ECG changes associated with prior Myocardial Infarction:
Any Q wave in leads V2–V3≥0.02 seconds or QS complex in leads V2 and V3
Q-wave≥0.03 seconds and ≥0.1 mV deep or QS complex in leads I, II, aVL, aVF, or V4-V6 in any two leads of a contiguous lead grouping (I, aVL, V6, V4-V6, II, III, and aVF)
R-wave≥0.04 seconds in V1-V2 and R/S≥1 with a concordant positive T-wave in the absence of a conduction defect Criterion for Reinfarction: In patients where recurrent MI is suspected from clinical signs or symptoms following the initial infarction, an immediate measurement of the employed cardiac biomarker is recommended. A second sample should be obtained 3-6 hours later. Recurrent infarction is diagnosed if there is a ≥20% increase of the value in the second sample. This value should exceed the $99^{th}$ percentile URL. However if cardiac biomarkers are elevated prior to the suspected new MI, there must also be documentation of decreasing values (two samples at least 6 hours apart) prior to the suspected new MI. If the values are falling criteria for reinfarction by further measurement of biomarkers together with features of the ECG or imaging can be applied.

ECG diagnosis of reinfarction following the initial infarction: may be confounded by the initial evolutionary ECG changes. Reinfarction should be considered when the ST elevation ≥0.1 mV reoccurs in an inpatient having a lesser degree of ST elevation or new pathognomonic Q-waves, in at least two contiguous leads, particularly when associated with ischemic symptoms for 10 minutes or longer, The re-evaluation of the ST segment can, however also be seen in threatening myocardial rupture and should lead to additional diagnostic work-up. ST depression or LBBB on their own should not be considered valid criteria for Myocardial Infarction.

If biomarkers are increasing or peak is not reached then there is insufficient data to diagnose recurrent MI.

Clinical Classification of different types of Myocardial Infarction: for each MI identified a Type of MI will be assigned using the following guidelines:
Type 1—Spontaneous MI related to ischemia due to a primary coronary event such as plaque erosion and/or rupture, fissuring or dissection.
Type 2—MI secondary to ischemia due to either increased oxygen demand or decreased supply, e.g. coronary artery spasm, anemia, hypotension, coronary embolism, arrhythmias, hypertension or hypotension.
Type 3—Sudden unexpected cardiac death including cardiac arrest, often with symptoms suggestive of myocardial ischemia accompanied by presumably new ST elevation, or new LBBB, or evidence of fresh thrombus in a coronary artery by angiography and/or at autopsy, but death occurring before blood samples could be obtained or at a time before the appearance of cardiac biomarkers in the blood.
Type 4a—MI associated with PCI.
Type 4b—MI associated with stent thrombosis as documented by autopsy or angiography.
Type 5—MI associated with CABG.

The term "silent MI": the following criteria will be used by the central ECG reading vendor to define interval "silent" (no clinical symptoms or signs) MI between baseline and yearly ECGs:

Criteria for MI (Surawcz, Ed: Chou's Electrocardiography in Clinical Practice, 5th Edition, 2001).

Myocardial infarctions are reported only on the basis of pathologic Q waves. Pathologic Q waves are defined as Q wave duration >40 ms and Q/R ratio=⅓.

Any Q wave in V1 or V2 that is followed by an R wave should be considered abnormal.

When pathologic Q waves (i.e., myocardial infarction) are present, ST elevation or T wave inversion may be used to classify the infraction as New or Acute. However, ST elevation or T wave inversion in the absence of pathologic Q waves are not sufficient criteria for diagnosis of myocardial infarction.

Anterolateral MI—Pathologic Q waves in leads V3-V6.
Anterior MI—Pathologic Q waves in V3 and V4.
Anteroseptal MI—Pathologic Q waves or QS in leads V1-V4.
Extensive Anterior MI—Pathologic Q waves in leads I, aVL, and V1-V6.

High lateral MI—Pathologic Q waves in leads I and aVL.
Inferior MI—Pathologic Q waves or QS in at least two of the inferior leads: aVF, III, II.
Lateral MI—Pathologic Q waves in leads I, aVL, and V5-V6.
Septal MI—Pathologic Q waves or QS in leads V1-V2, (V3). In the presence of LAHB or LVH a Q or QS in V3 is required.
Posterior MI—Initial R wave duration 40 ms in V1 or V2, and R>S and upright T wave; Inferior or Lateral MI are usually also present.

The term "new MI" These criteria for MI are more stringent than the Expert Consensus Document criteria, requiring Q waves to be ≥0.04 sec in duration and an R/S ratio ≥⅓. These criteria (drawn from the cardiology literature) are designed to minimize the false positive detection of MIs due to very small physiologic Q waves in the inferior and anterolateral leads.

As used herein, the term "stroke" is defined as the rapid onset of a new persistent neurological deficit attributed to an obstruction in cerebral blood flow and/or cerebral hemorrhage with no apparent non-vascular cause (e.g. tumor, trauma, infection). Available neuroimaging studies will be considered to support the clinical impression and to determine if there is a demonstrable lesion compatible with an acute stroke. Non-fatal strokes will be classified as ischemic, hemorrhagic or unknown.

As used herein the term "stent thrombosis" is defined as follows:

| Type | Timing |
| --- | --- |
| Acute stent thrombosis* | 0 to 24 hours after stent implantation |
| Subacute stent thrombosis | >24 hours to 30 days after stent implantation |
| Late stent thrombosis† | >30 days to 1 year after stent implantation |
| Very late stent thrombosis† | >1 year after stent implantation |

Stent thrombosis should be reported as a cumulative value over time and at the various individual time points specified above. Time 0 is defined as the time point after the guiding catheter has been removed and the patient has left the catherization laboratory.
*Acute or subacute can also be replaced by the term early stent thrombosis. Early stent thrombosis (0 to 30 days) will be used in the remainder of this document.
†Includes primary as well as secondary late stent thrombosis; secondary late stent thrombosis is a stent thrombosis after a target lesion revascularization.

"Definite stent thrombosis" refers to a stent thormbosis considered to have occurred by either angiographic or pathological confirmation.

Angiographic confirmation of stent thrombosis:
The presence of a thrombus that originates in the stent or in the segment 5 mm proximal or distal to the stent and presence of at least 1 of the following within a 48 hour time window: acute onset of ischemic symptoms at rest, new ischemic ECG changes that suggest acute ischemia, typical rise and fall in cardiac biomarkers, non-occlusive thrombus, occlusive thrombus.

Pathological confirmation of stent thrombosis:
Evidence of recent thrombosis within the stent determined at autopsy or via examination of tissue retrieved following thrombectomy.

The term "probable stent thrombosis" refers to stent stenosis which is considered to have occurred after intracoronary stenting in the following cases: any unexplained death within the first 30 day, or irrespective of the time after the index procedure, any MI that is related to documented acute ischemia in the territory of the implanted stent without angiographic confirmation of stent thrombosis and in the absence of any other cause.

As used herein the term "unstable angina requiring unplanned revascularization" is defined as no elevation in cardiac biomarkers and clinical presentation (one of the following) with cardiac symptoms lasting ≥10 minutes and considered to be myocardial ischemia on final diagnosis (rest angina or new onset (<2 months) severe angina (CCS classification severity≥III; Grading of Angina Pectoris According to Canadian Cardiovascular Society Classification) or increasing angina (in intensity, duration and/or frequency) and severe recurrent ischemia requiring urgent revascularization: as defined by an episode of angina prompting the performance of coronary revascularization on the index hospitalization or an episode of recurrent angina after discharge that resulted in re-hospitalization during which coronary revascularization was performed; and at least one of the following: new or worsening ST or T segment changes on ECG, ST Elevation (new ST elevation at the J point in two anatomically contiguous leads with the cut-off points: ≥0.2 mV in men (>0.25 mV in men <40 years) or ≥0.15 mV in women in leads V2-V3 and/or ≥0.1 mV in other leads), ST depression and T-wave Evidence of ischemia on stress testing with cardiac imaging, evidence of ischemia on stress testing without cardiac imaging but with angiographic evidence of ≥70% lesion, and/or thrombus in the epicardial coronary artery or initiation/increased dosing of anti-anginal therapy, angiographic evidence of ≥70% lesion and/or thrombus in an epicardial coronary artery.

As used herein, the term "heart failure requiring hospitalization" is defined as an event that meets the following criteria:

Requires hospitalization defined as an admission to an inpatient unit or a visit to an emergency department that results in at least a 12 hour stay (or a date change if the time of admission/discharge is not available) AND clinical manifestation of heart failure including at least one of the following: New or worsening: dyspnea, orthopnea, paroxysmal nocturnal dyspnea, edema, pulmonary basilar crackles, radiological evidence of worsening heart failure AND additional/increased therapy (initiation of IV loop diuretic, inotrope or vasodilator therapy, uptitration of IV therapy; if already on therapy initiation of mechanical or surgical intervention, or use of ultra-filtration, hemofiltration or dialysis that is specifically directed at the treatment of heart failure).

Biomarker results (e.g. brain natriuretic peptide) consistent with congestive heart failure will be supportive of this diagnosis.

As used herein, the term "prediabetes" is defined as the state in which some but not all of the diagnostic criteria for diabetes are met. It is often described as the "gray area" between normal blood sugar and diabetic levels. While in this range, patients are at risk for not only developing type 2 diabetes, but also for cardiovascular complications. Prediabetes is also referred to as borderline diabetes, impaired glucose tolerance (IGT), and/or impaired fasting glucose (IFG).

As used herein the term "new onset diabetes" (NOD) refers to:

The clinical definition of Type 2 diabetes consists of the following

Presence of Fasting Plasma Glucose measured on two consecutive occasions ≥126 mg/dl within 6 weeks (the Event Date will be the first of these two occasions), or presence of HbA1c measured on two consecutive occasions ≥6.5% within 6 weeks in a laboratory which has validated compliance of a test that conforms to the National Glycosylation Standards Program (Little et al 2010) reference measurement of HbA1c (the Event Date will be the first of these two occasions), or the institution and use of a diabetes medication for the purpose of glucose control by the patient including all oral agents, insulin, and injectable GLP-1 analogs.

In the event wherein a patient has one laboratory parameter which would place them in the NOD category if repeated and confirmed within 6 weeks, then has a subsequent measurement another parameter which similarly would place them in the NOD category if repeated and confirmed within 6 weeks (e.g. FPG≥126 mg/dl followed by HbA1c≥6.5%, or vice versa) will be considered to have NOD (the Event Date will be the first of these 2 occasions).

As used herein the term "transient ischemic attack" is defined as change in the blood supply to a particular area of the brain, spinal cord, or retina, resulting in brief neurologic dysfunction that persists, by definition, for less than 24 hours.

New and focal neurologic sensory and/or motor deficits, which have a rapid onset, last no more than 24 hours and resolve completely. Symptoms may be localized to brain, spinal cord, or retina, relative to the vascular supply affecting neurologic function.

Focal sensory, reflexes, and motor lesions, which are manifestations of the arterial structure from which the insufficiency arises. All new neurologic signs resolve completely within 24 hours from the time of onset (hemiplegia/paresis, hemianaesthesia/sensory deficit, hemianopsia, neglect, isolated facial weakness/droop, ataxia/dysmetria, dysarthria/speech impairment, aphasia or other.

A CT, MRI, or MRA of the brain, which demonstrates no new pathology. A neurological or neurosurgical consultation may accompany the imaging study or studies, but is not required for the diagnosis of TIA.

As used herein the term "critical limb ischemia" is a manifestation of occlusive peripheral arterial disease that describes patients with chronic occlusive disease who demonstrate ischemic rest pain or ischemic skin lesions (either ulcers or gangrene).

Pain at rest, claudication, recurrent skin lesions are common. Coolness to touch and pallor of the involved extremity may be present. Diminution or absence of pulse to palpation or bedside Doppler examination. Ulcers of the skin may be present.

CT, MRI, MRA or angiography may be performed for diagnostic purposes. Angiographic or open revascularization may be attempted to improve arterial blood flow.

The term "limb amputation due to vascular cause" refers to therapeutic resection of a limb or a portion of a limb due to a combination of vascular insufficiency, osteomyelitis, cellulitis/gangrene, or poor wound healing.

Symptoms may include claudication, rest pain, fever, and recurrent infections. There may be a history of previous partial or complete amputations.

Signs may include decreased arterial pulse, abnormal temperature, deformity, chronic skin ulceration.

Therapeutic resection of the pathologic extremity: Reasons for amputation may be vascular insufficiency, osteomyelitis, cellulitis, gangrene, poor healing post-surgical wound, poor healing post trauma.

As used herein the term "non-coronary revascularization" is defined as vascular surgery or percutaneous intervention. Vascular surgery is defined as the placement of a conduit with or without proximal and/or distal anastamoses. Percutaneous intervention is defined as balloon inflation with or without stenting.

Symptoms will be specific to the arterial vasculature involved and the time of course of development of the occlusion(s).

Signs will be specific to the arterial vasculature involved and the time of course of development of the occlusion(s).

Diagnostic CT, MRI, MRA, or Doppler US may be performed.

Revascularization or attempted revascularization with or without stenting including carotid surgery, peripheral vascular surgery or PCI, including abdominal aortic aneurysm repair, carotid revascularization, femoral, popliteal iliac, renal, open or percutaneous peripheral interventions depending on the site definition of supraventricular tachycardia/atrial fibrillation Supraventricular tachycardia includes abnormal sinus tachycardia, ectopic atrial tachycardia atrial fibrillation/atrial flutter (with rapid ventricular response) and junctional tachycardia.

As used herein "deep vein thrombosis" (DVT) is defined as the pathologic presence of thrombus with inflammation, which affects the leg veins (such as the femoral vein or the popliteal vein), the deep veins of the pelvis, or rarely an upper extremity vein.

There may be no symptoms referable to the location of the DVT, but the classical symptoms of DVT include pain, swelling and redness of the leg and dilation of the surface veins DVT include pain, swelling and redness of the leg and dilation of the surface veins may be present. Homan's sign, posterior calf pain on foot dorsiflexion may be present but is an insensitive indicator. Commonly, no signs are present.

Duplex ultrasonography is the most commonly used diagnostic test. Other tests may include d-dimer blood testing, CT with contrast, and infrequently venography. Confirmation by diagnostic study required.

As used herein, a "pulmonary embolism" is defined as an acute blockage of one or more pulmonary arteries by an embolus, which has originated elsewhere (usually venous thrombus) and traveled through the venous system to reach the pulmonary arteries.

Symptoms may include sudden-onset dyspnea, tachypnea, chest pleuritic chest pain, cough, and hemoptysis. In addition, severe cases can include signs such as cyanosis, tachycardia, hypotension, and syncope.

Chest X-Rays may be performed but are rarely diagnostic. Blood testing for d-dimer is often used to screen prior to performing medical imaging. Spiral CT of the chest is often performed. If significant pathology makes spiral CT less useful, a ventilation perfusion scan of the chest may be available. Confirmation by diagnostic study and localization (left or right lung and lobe) required.

A used herein "coronary angiography" is an invasive procedure wherein radiocontrast dye is introduced via an arterial catheter into the aorta, left ventricle, and coronary arteries to examine the functional capacity and anatomy of these entities.

A radiocontrast dye is administered as described above by a cardiologist or invasive radiologist, using peripheral access into an artery (femoral or brachial).

As used herein "coronary revascularization" is defined as an invasive procedure, which usually follows coronary angiography, wherein either percutaneous transluminal intervention, followed by Stent Placement, Balloon Angioplasty, or CABG is performed to relieve obstructed coronary arteries. A team of medical professionals lead by either an invasive cardiologist (percutaneous transluminal intervention, followed by stent placement, balloon angioplasty) or a thoracic surgeon (CABG), who performs the described procedures.

As used herein, supraventricular tachycardia (SVT)/atrial fibrillation includes abnormal sinus tachycardia, ectopic atrial tachycardia atrial fibrillation/atrial flutter (with rapid ventricular response) and junctional tachycardia.

Symptoms may include palpitations, dyspnea, chest pain, dizziness, numbness or loss of consciousness. Signs may include rapid heart rate, which may be regular or irregular. Peripheral pulses may be diminished or absent.

ECG demonstrates narrow complex tachycardia originating from a site (or sites) above the ventricles. P waves may or may not be present, depending on the specific type of SVT.

Patient Reported Outcome Measures: EQ-5D

Generic multidimensional health-related quality of life will be assessed with the EuroQoL™ (EQ-5D). The EuroQoL™ EQ-5D is a simple but effective standardized instrument designed for use as a measure of health outcome. Applicable to a wide range of health conditions and treatments, it provides both a compact descriptive profile and a single index value that can be used in the clinical and economic evaluation of health care.

The EQ-5D measures five domains (mobility, self-care, usual activity, pain/discomfort & anxiety/depression). There are two parts to this questionnaire.

The first, 'health state classification' consists of five questions.

The second, 'Visual Analogue Scale Thermometer' consists of a visual analogue scale.

This generates a self-rating of current health-related quality of life. This will be used with the health state classification to build a composite picture of the respondent's health status.

Data Capture:

EQ-5D enables an accurate self-description of current health-related quality of life to be easily recorded. Self-explanatory instructions to respondents are provided within the questionnaire and it takes about two minutes to complete.

Health State Classification: The first page consists of five questions. The respondent is asked to indicate his/her current health state, by ticking the most appropriate of three statements about each of the five quality of life dimensions. Each statement represents an increasing level of severity (1=no problem, 2=some or moderate problem, 3=unable or extreme problem). For example, a respondent with 'no problem' for each of the five questions will be said to have a health status of 11111.

Visual Analogue Scale 'Thermometer': The 'Thermometer' has end points of 100 (best imaginable health state) at the top and 0 (worst imaginable health status) at the bottom. The respondent will rate his/her current health status by drawing a line from the box marked 'Your health status today' to the appropriate point on the 'thermometer' scale.

The site staff should record the two digits reading on the thermometer (where the line by the respondent crosses the thermometer) on the appropriate space in the CRF. Missing or ambiguous values will be left blank.

Example 1: A Randomized, Double-Blind, Placebo-Controlled, Event-Driven Trial of Quarterly Subcutaneous Canakinumab in the Prevention of Recurrent Cardiovascular Events Among Stable Post-myocardial Infarction Patients with Elevated hsCRP This study is a Phase 3, multi-center, randomized, parallel group, placebo-controlled, double-blind event-driven clinical trial.

Screening will take place no earlier than:
28 days after the index MI and on stable long term medication.
28 days after a PCI if it was during a different hospital admission than the qualifying MI. Screening can only be initiated following this procedure.
3 years post a CABG procedure regardless of timing of the qualifying MI.

Rationale of Study Design

This study has been designed as a multi-center, randomized, parallel group, placebo-controlled, double-blind, event-driven trial to provide definitive evidence on the effects of canakinumab on cardiovascular adverse events in patients with recent MI and elevated inflammatory burden as evidenced by elevated hsCRP. This study will also measure the effects of canakinumab on the conversion to NOD as a secondary endpoint. This study design is the most robust clinical trial design to test the hypothesis that anti-inflammatory treatment with canakinumab will reduce major adverse cardiovascular events. The study design is shown in FIG. 9.

Rationale of Dose/Regimen, Duration of Treatment

Canakinumab in doses starting from 25 mg to 300 mg with increments of 5 mg will be used to select the optimal dose regarding to the risk-benefit ratio for various subgroups of post-myocardial infarction patients e.g. elderly patients when necessary. Further, this dosing interval facilitates adjustment of doses for factors influencing pharmacokinetic parameters e.g. body weight to maintain blood concentrations of canakinumab at optimal level when necessary.

Canakinumab 50 mg and 150 mg Quarterly

The 50 mg and 150 mg canakinumab dosing schedule has been selected on the basis of anticipated efficacy, safety, and biomarker modeling data. In phase II development, all canakinumab doses up to 300 mg subcutaneous (s.c.) every other week have been found safe, well tolerated, and free of adverse lipid effects. Canakinumab efficacy in lowering hsCRP, IL-6 and fibrinogen was assessed based on studies CACZ885A2213 and CACZ885I2202. The maximum efficacy of hsCRP lowering in study CACZ885I2202 was at approximately 50-75 mg of canakinumab monthly, with persistent lowering across a wide range of higher doses. Therefore, 50 mg monthly as fully efficacious dose and 15 mg monthly as submaximal dose were selected for further development (see FIG. 6). The optimal dosing interval was examined using data from CACZ885A2213 (diabetes) and from gout studies with canakinumab (see FIG. 4). These studies indicated that canakinumab effect on lowering hsCRP was durable for up to approximately 3 months (see FIG. 3). Further, modeling and simulation methods showed that 150 mg quarterly dosing had similar free IL-1β suppression compared to 50 mg monthly dosing and 50 mg quarterly dosing had similar free IL-1β suppression compared to 15 mg monthly dosing. This conclusion was reached by comparing the doses and regimens based on both the time for maintenance of suppression and the fraction of patients below a specified suppression threshold of 'tissue free' IL-1β. Therefore, canakinumab 50 mg and 150 mg quarterly administration were selected for the doses in this study, CACZ885M2301. The selected doses allow examination canakinumab dose response in preventing recurrent cardiovascular events and to determine if a lower dose than 150 mg would have a favorable risk benefit ratio.

Canakinumab 300 mg Quarterly

Given evidence of safety across a wide dosing range, a 300 mg quarterly dosing schedule for canakinumab has also been developed for CACZ885M2301. This allows evaluation of a higher canakinumab dose since the dose needed for adequate IL-1β neutralization within the plaque or systemically in inflammation-based atherosclerosis is not established. Therefore, a higher dose may deliver greater efficacy than the other selected dose, 150 mg quarterly. This 300 mg quarterly dosing regimen also includes an induction period over 2 weeks, dosing at randomization (month 0) and at week 2 (month 0.5), in order to assure that auto-induction of IL-1β pathway is adequately inhibited at study initiation. The complete suppression of IL-1β related gene expression achieved with this early high dose administration, coupled with the continuous canakinumab treatment effect which has been proven to last the entire quarterly dosing period, is expected to minimize the potential for IL-1β rebound. This may be relevant for pathogenesis of atherosclerosis because it is theorized that IL-1 auto-induction provides a positive feedback mechanism for vascular disease including atherosclerosis. The lower 50 mg and 150 mg quarterly doses does not include an early high, induction dose regimen to ensure separation of the three canakinumab dose levels included in this protocol and to allow assessment of the impact of the early high dose regimen included in the 300 mg arm on clinical cardiovascular events.

In phase II studies in patients with gout, diabetes, and acute inflammatory conditions, safety of canakinumab across a wide range of doses has not emerged as a major clinical issue. Due to long term suppression of inflammatory biomarkers, quarterly dosing of canakinumab is feasible and likely to be clinically effective. In addition, data in the setting of acute inflammation suggests that higher initial doses of canakinumab that can be achieved through induction are safe and provide an opportunity to ameliorate concern regarding potential auto-induction of IL-1β and to achieve greater early suppression of IL-1β related gene expression.

IL-1β auto-induction has been shown in human mononuclear blood, human vascular endothelial, and vascular smooth muscle cells in vitro and in rabbits in vivo where IL-1 has been shown to induce its own gene expression and circulating IL-1β level (Dinarello et al. 1987, Warner et al. 1987a, and Warner et al. 1987b). These studies suggested that IL-1 induced IL-1 gene expression may provide a positive feedback mechanism in the pathogenesis of atherosclerosis and promote atherosclerosis. This consequently suggests that suppression of this feedback mechanism may provide benefits in the atherosclerotic lesion. Specifically, data supporting an induction dose of canakinumab includes the following: In CACZ885A2102, a CAPS mechanism of action study of patients with Muckle Wells Syndrome (N=4), canakinumab treatment with 10 mg/kg i.v. (equivalent to 600 mg i.v.) single dose induced clinical (improved skin lesions and conjuctival injection) and biomarker (hsCRP and SAA) responses in 24 hrs which was durable up to 180 days. In contrast, canakinumab doses of 1 mg/kg i.v. without induction were only durable up to 90 days. Support for more sustained and higher dose canakinumab therapy was also seen in the rheumatoid arthritis proof of concept study CACZ885A2101, where higher doses of canakinumab were required (≥3.0 mg/kg i.v.) to achieve a significant clinical response as scored by the ACR system. Furthermore, in the CACZ885A2102 study, analysis of gene expression known to be related to IL-1 β expression, inflammasome activity, and autoinduction of IL-1β, showed more complete response to higher dose (10 mg/kg i.v.) than lower dose (1 mg/kg i.v.) canakinumab. In addition, IL-1β and inflammasome related gene expression modification began to decrease with the lower dose (1 mg/kg i.v.) compared to the higher dose (10 mg/kg i.v.) between 10 and 12 weeks. Similar results were obtained in a canakinumab rheumatoid arthritis study where IL-1β related genes were suppressed more with 300 mg s.c. q2weeks dosing than 150 mg q4weeks dosing.

The documented safety record of canakinumab up to doses of 300 mg s.c. every 2 weeks with and without induction dose of 600 mg i.v., in a study in rheumatoid arthritis patients up to 6 months, 300 mg q1month, in a study in gout patients up to 6 months, and 150 mg q1month, in a study in T2DM patients up to 4 months supports the use of this higher dose regimen.

Rationale for Choice of Comparator

This trial is placebo controlled to provide robust evidence on the effects of canakinumab on clinical events and safety as well tolerability. No comparative anti-inflammatory treatment has been shown to date to benefit patients with cardiovascular disease and thus an active comparator arm is not available. All patients in all treatment arms will receive standard of care post-MI background therapy including, but not limited to, lipid lowering, anti-hypertensive, beta blockers, and anti-platelet therapy as appropriate.

Objectives of the study are the prevention or reduction of risk of major adverse cardiovascular event (MACE) occurring during the double-blind treatment period, which is a composite of CV death, non-fatal MI, and stroke.

Other objectives are hospitalization for unstable angina requiring unplanned, new onset type-diabetes among patients with pre-diabetes at randomization, deep-vein thormbosis/pulmonary embolism, Supraventricular tachycardia/atrial fibrillation, stent thrombosis (probable or definite), hospitalization or prolongation of hospitalization for heart failure, cardiovascular death, non-fatal MI, stroke and all-cause mortality composite, major coronary events composite (CHD death, non-fatal MI), total vascular events composite, coronary revascularization procedures (PCI or coronary artery bypass graft (CABG) and stroke by etiology Patient reported outcomes (PRO) have been identified as important in the post MI patient population. While a variety of relevant concepts within the context of canakinumab have been identified, the concepts of tiredness, physical function and performance function have been selected as prioritized measurement concepts. In order to measure these concepts a set of PRO instruments will be administered.

The PRO instrument to be included in this trial, where available, is the EQ-5D. Details on each of this instrument are provided in addition to the target population in the sections "General".

REFERENCES

Bird R E, Hardman K D, Jacobson J W, Johnson S, Kaufman B M, Lee S M, Lee T, Pope S H, Riordan G S, Whitlow M (1988). Single-chain antigen-binding proteins. Science, October 21; 242(4877):423-6.

Brannath W, Bretz F (2010) Shortcuts for locally consonant closed test procedures. J American Statistical Association: 105(490): 660-9.

Bretz F, Maurer W, Brannath W, et al (2009 A graphical approach to sequentially rejective multiple test procedures. Statistics in Medicine; 28(4): 586-604.

Cannon C P, Braunwald E, McCabe C H, et al (2004) Pravastatin or Atorvastatin Evaluation and Infection Therapy—Thrombolysis in Myocardial Infarction 22 Investigators: Intensive versus Moderate Lipid Lowering with Statins after Acute Coronary Syndromes. NEJM; 350:1495-504.

Cox D R (1972) Regression models and life-tables (with discussion). J. R. Statist. Soc, B; 34:187-220.

Diabetes Prevention Program Research Group (2002) Reduction in the incidence of type 2 diabetes with lifestyle intervention or metformin. NEJM; 346:393-403.

Dinarello C, Ikejima T, Warner S J C, et al (1987) Interleukin 1 induces interleukin 1, I. Induction of circulating interkeukin tin rabbits in vivo and in human mono nuclear cells in vitro. J. Immunol; 139: 1902-1910.

Duewell P, Kono H, Rayner K J, et al (2010) NLRP3 inflammasomes are required for atherogenesis and activated by cholesterol crystals. Nature; 464(7293):1357-61.

Dunnett C W (1955) A multiple comparison procedure for comparing several treatments with a control. J American Statistical Association; 50:1096-1121.

European Society of Hypertension (2003) European Society of Cardiology guidelines for the management of arterial hypertension. Journal of Hypertension; 21:1011-1053.

Hochberg Y (1988) A sharper Bonferroni procedure for multiple tests of significance. Biometrika; 75:800-2.

Holm S (1979) A simple sequentially rejective multiple test procedure. Scan J Statist 6:65-70.

Huston J S, Levinson D, Mudgett-Hunter M, Tai M S, Novotný J, Margolies M N, Ridge R J, Bruccoleri R E, Haber E, Crea R, et al. (1988) Protein engineering of antibody binding sites: recovery of specific activity in an anti-digoxin single-chain Fv analogue produced in Escherichia coli. Proc Natl Acad Sci USA. 85: 5879-83.

Kaptoge S, Di Angeloantonio E, Lowe G et al Emerging Risk Factors Collaboration (2010) C-reactive protein concentration and risk of coronary heart disease, stroke and mortality: an individual meta-analysis. Lancet; 375:132-140.

Knappik A, Ge L, Honegger A, Pack P, Fischer M, Wellnhofer G, Hoess A, Wölle J, Plückthun A, Virnekäs B (2000). Fully synthetic human combinatorial antibody libraries (HuCAL) based on modular consensus frameworks and CDRs randomized with trinucleotides. J Mol Biol.; 296: 57-86.

Lan G, DeMets D (1983) Discrete sequential boundaries for clinical trials. Biometrika 70(3):659-663.

Little R R (2010) Consensus Statement on the Worldwide Standardization of HbA1c (Internet) Available from <http://www.ngsp.org/contact.asp> (Accessed 22 Sep. 2010)

Mancia G, Laurent S, Agabiti-Rosei E et al (2009) Reappraisal of European guidelines on hypertension management: a European Society of Hypertension Task Force document. J Hypertension; 27: 1-38.

McMurray J J, Kjekshus J, Gullestad L et al (2009) Effects of statin therapy according to plasma high-sensitivity C-reactive protein concentration in the controlled rosuvastatin multinational trial in heart failure (CORONA), Circulation; 120: 2188-2196.

Morrow D A, de Lemos J A, Sabatine M S, et al (2006) Clinical relevance of C-reactive protein during follow-up of patients with acute coronary syndromes in the Aggrastat-to-Zocor trial. Circulation; 114: 281-288.

O'Connor C M, Dunne M W, Pfeffer M A, et al (2003) Azithromycin for the Secondary Prevention of Coronary Heart Disease Events: The WIZARD Study: A Randomized Controlled Trial. JAMA; 290(11):1459-1466.

Peto R (1972) Discussion on Professor Cox's Paper. J. R. Statist. Soc., B; 34:205-207.

Ridker P M, Danielson E, Fonseca F A, et al (2008) Rosuvastatin to prevent vascular events in men and women with elevated C-reactive protein. NEJM; 359: 2195-2207.

Ridker P M, Danielson E, Fonseca F A, et al (2009) Reduction in C-reactive protein and LDL cholesterol and cardiovascular event rates after initiation of rosuvastatin: a prospective study of the JUPITER trial. Lancet; 373: 1175-82.

Ridker P M, Cannon C P, Morrow D, et al (2005) C-Reactive Protein Levels and Outcomes after Statin Therapy, NEJM; 352:20-8.

Ridker P M, Rifai N, Clearfield M, et al (2001) Measurement of C-reactive protein for the targeting of statin therapy in the primary prevention of acute coronary events, NEJM; 344:1959-1965.

Ridker P M, Rifai N, Pfeffer M A, et al (1998) Inflammation, pravastatin, and the risk of coronary events after myocardial infarction in patients with average cholesterol levels. Cholesterol and Recurrent Events (CARE) Investigators. Circulation; 98: 839-44.

Tardif J-C, McMurray J J V, Klug E et al (2008) Effects of succinobucol (AGI-1067) after an acute coronary syndrome: a randomized, double-blind, placebo-controlled trial. Lancet; 371: 1761-8.

Thygesen, K, Alpert, J S, White, H D et al (2007). Universal Definition of Myocardial Infarction. Circulation; 116: 2634-2653.

Ward E S, Güssow D, Griffiths A D, Jones P T, Winter G (1989). Binding activities of a repertoire of single immunoglobulin variable domains secreted from Escherichia coli. Nature.; 34: 544-6.

Warner S J C, Auger K R, and Libby P (1987a). Human interleukin 1 induces interleukin 1 gene expression in human vascular smooth muscle cells. J. Exp. Med; 165: 1316-1331.

Warner S J C, Auger K R, and Libby P (1987b) Human interleukin 1 induces interleukin 1. II. Recombinant human interkeukin 1 induces interleukin 1 production by adult human vascular endothelial cells. J. Immunol; 139: 1911-1917.

BOOK REFERENCES

Allison P D (1995) Survival analysis using the SAS® System: A Practical Approach, Cary, N C: SAS Institute Inc.

Chou's Electrocardiography in Clinical Practice; Surawicz, B, Knilans, T; Ed. 5$^{th}$ Edition. (2001). Saunders Publishing. Literature available on request.

Genz A, Bretz F (2009). Computation of multivariate normal and t probabilities. Lecture Notes in Statistics, Vol. 195. Springer, Heidelberg.

The invention claimed is:

1. A method of reducing the risk of experiencing cardiovascular death in a stable patient who has had a prior myocardial infarction (MI), the method comprising subcutaneously administering 150 mg-300 mg of an IL-1β binding antibody or functional fragment thereof to the patient at week 0 and then every three months thereafter beginning at week 12, wherein the patient has an hsCRP level of ≥1 mg/L before administration of the IL-1β binding antibody or functional fragment thereof, and wherein the IL-1β binding antibody or functional fragment thereof comprises:
   a) the three complimentary determining regions (CDRs) set forth as SEQ ID NO: 3, SEQ ID NO: 4, and SEQ ID NO: 5, and the three CDRs set forth as SEQ ID NO: 6, SEQ ID NO: 7, and SEQ ID NO: 8; or
   b) a $V_H$ domain comprising SEQ ID NO: 1 and a $V_L$ domain comprising SEQ ID NO: 2.

2. The method of claim 1, wherein the method comprises administering 300 mg of the IL-1β binding antibody or functional fragment thereof.

3. The method of claim 1, wherein the first dose of the IL-1β binding antibody or functional fragment thereof is administered no earlier than 28 days after the prior MI.

4. The method according to claim 1, wherein the IL-10 binding antibody or functional fragment thereof is canakinumab.

5. The method according to claim 1, wherein the IL-1β binding antibody or functional fragment thereof is capable of inhibiting the binding of IL-1β to its receptor and has a $K_D$ for binding to IL-1β of 50 pM or less.

6. The method according to claim 1, wherein the IL-1β binding antibody or functional fragment thereof is additionally administered to the patient at week 2.

7. The method of claim 1, wherein the patient has an hsCRP level of ≥2 mg/L before administration of the IL-1β binding antibody or functional fragment thereof.

8. A method of reducing the risk of experiencing stroke in a stable patient who has had a prior myocardial infarction (MI), the method comprising subcutaneously administering 150 mg-300 mg of an IL-1β binding antibody or functional fragment thereof to the patient at week 0 and then every three months thereafter beginning at week 12, wherein the patient has an hsCRP level of ≥1 mg/L before administration of the IL-1β binding antibody or functional fragment thereof, and wherein the IL-1β binding antibody or functional fragment thereof comprises:
   a) the three complimentary determining regions (CDRs) set forth as SEQ ID NO: 3, SEQ ID NO: 4, and SEQ ID NO: 5, and the three CDRs set forth as SEQ ID NO: 6, SEQ ID NO: 7, and SEQ ID NO: 8; or
   b) a $V_H$ domain comprising SEQ ID NO: 1 and a $V_L$ domain comprising SEQ ID NO: 2.

9. The method of claim 8, wherein the method comprises administering 300 mg of the IL-1β binding antibody or functional fragment thereof.

10. The method of claim 8, wherein the first dose of the IL-1β binding antibody or functional fragment thereof is administered no earlier than 28 days after the prior MI.

11. The method according to claim 8, wherein the IL-1β binding antibody or functional fragment thereof is canakinumab.

12. The method according to claim 8, wherein the IL-1β binding antibody or functional fragment thereof is capable of inhibiting the binding of IL-1β to its receptor and has a $K_D$ for binding to IL-1β of 50 pM or less.

13. The method according to claim 8, wherein the IL-1β binding antibody or functional fragment thereof is additionally administered to the patient at week 2.

14. The method of claim 8, wherein the patient has an hsCRP level of ≥2 mg/L before administration of the IL-1β binding antibody or functional fragment thereof.

15. A method of reducing the risk of experiencing myocardial infarction (MI) in a stable patient who has had a prior MI, the method comprising subcutaneously administering 150 mg-300 mg of an IL-1β binding antibody or functional fragment thereof to the patient at week 0 and then every three months thereafter beginning at week 12, wherein the patient has an hsCRP level of ≥1 mg/L before administration of the IL-1β binding antibody or functional fragment thereof, and wherein the IL-1β binding antibody or functional fragment thereof comprises:
   a) the three complimentary determining regions (CDRs) set forth as SEQ ID NO: 3, SEQ ID NO: 4, and SEQ ID NO: 5, and the three CDRs set forth as SEQ ID NO: 6, SEQ ID NO: 7, and SEQ ID NO: 8; or
   b) a $V_H$ domain comprising SEQ ID NO: 1 and a $V_L$ domain comprising SEQ ID NO: 2.

16. The method of claim 15, wherein the method comprises administering 300 mg of the IL-1β binding antibody or functional fragment thereof.

17. The method of claim 15, wherein the first dose of the IL-1β binding antibody or functional fragment thereof is administered no earlier than 28 days after the prior MI.

18. The method according to claim 15, wherein the IL-1β binding antibody or functional fragment thereof is canakinumab.

19. The method according to claim 15, wherein the IL-1β binding antibody or functional fragment thereof is capable of inhibiting the binding of IL-1β to its receptor and has a $K_D$ for binding to IL-1β of 50 pM or less.

20. The method according to claim 15, wherein the IL-1β binding antibody or functional fragment thereof is additionally administered to the patient at week 2.

21. The method of claim 15, wherein the patient has an hsCRP level of ≥2 mg/L before administration of the IL-1β binding antibody or functional fragment thereof.

* * * * *

SEQUENCE LISTING

<160> NUMBER OF SEQ ID NOS: 8

<210> SEQ ID NO 1
<211> LENGTH: 118
<212> TYPE: PRT
<213> ORGANISM: homo sapiens

```
<400> SEQUENCE: 1

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Gly Met Asn Trp Val Arg Gln Ala Pro Gly Lys Gly Leu Glu Trp Val
        35                  40                  45

Ala Ile Ile Trp Tyr Asp Gly Asp Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Asp Leu Arg Thr Gly Pro Phe Asp Tyr Trp Gly Gln Gly Thr
            100                 105                 110

Leu Val Thr Val Ser Ser
            115

<210> SEQ ID NO 2
<211> LENGTH: 107
<212> TYPE: PRT
<213> ORGANISM: homo sapiens

<400> SEQUENCE: 2

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Phe
                85                  90                  95

Thr Phe Gly Pro Gly Thr Lys Val Asp Ile Lys
            100                 105

<210> SEQ ID NO 3
<211> LENGTH: 5
<212> TYPE: PRT
<213> ORGANISM: HOMO SAPIENS

<400> SEQUENCE: 3

Val Tyr Gly Met Asn
1               5

<210> SEQ ID NO 4
<211> LENGTH: 17
<212> TYPE: PRT
<213> ORGANISM: HOMO SAPIENS

<400> SEQUENCE: 4

Ile Ile Trp Tyr Asp Gly Asp Asn Gln Tyr Tyr Ala Asp Ser Val Lys
1               5                   10                  15

Gly
```

```
<210> SEQ ID NO 5
<211> LENGTH: 6
<212> TYPE: PRT
<213> ORGANISM: HOMO SAPIENS

<400> SEQUENCE: 5

Asp Leu Arg Thr Gly Pro
1               5

<210> SEQ ID NO 6
<211> LENGTH: 11
<212> TYPE: PRT
<213> ORGANISM: HOMO SAPIENS

<400> SEQUENCE: 6

Arg Ala Ser Gln Ser Ile Gly Ser Ser Leu His
1               5                   10

<210> SEQ ID NO 7
<211> LENGTH: 6
<212> TYPE: PRT
<213> ORGANISM: HOMO SAPIENS

<400> SEQUENCE: 7

Ala Ser Gln Ser Phe Ser
1               5

<210> SEQ ID NO 8
<211> LENGTH: 7
<212> TYPE: PRT
<213> ORGANISM: HOMO SAPIENS

<400> SEQUENCE: 8

His Gln Ser Ser Ser Leu Pro
1               5
```